United States Patent
Knas et al.

(10) Patent No.: US 11,571,165 B1
(45) Date of Patent: Feb. 7, 2023

(54) SYSTEM AND METHOD FOR INGESTIBLE DRUG DELIVERY

(71) Applicant: MASSACHUSETTS MUTUAL LIFE INSURANCE COMPANY, Springfield, MA (US)

(72) Inventors: Michal Knas, Monson, MA (US); Jiby John, Suffield, CT (US)

(73) Assignee: MASSACHUSETTS MUTUAL LIFE INSURANCE COMPANY, Springfield, MA (US)

( * ) Notice: Subject to any disclaimer, the term of this patent is extended or adjusted under 35 U.S.C. 154(b) by 1066 days.

(21) Appl. No.: 16/128,230

(22) Filed: Sep. 11, 2018

Related U.S. Application Data

(60) Provisional application No. 62/556,978, filed on Sep. 11, 2017, provisional application No. 62/556,956, (Continued)

(51) Int. Cl.
  *A61B 5/00* (2006.01)
  *G16H 50/30* (2018.01)
  (Continued)

(52) U.S. Cl.
  CPC .............. *A61B 5/4848* (2013.01); *A61B 5/07* (2013.01); *A61B 5/073* (2013.01); *A61B 5/4839* (2013.01);
  (Continued)

(58) Field of Classification Search
  CPC .......... A61B 5/073; A61B 90/98; G16H 40/60
  See application file for complete search history.

(56) References Cited

U.S. PATENT DOCUMENTS

| | | | |
|---|---|---|---|
| 7,125,382 | B2 | 10/2006 | Zhou et al. |
| 8,721,540 | B2 | 5/2014 | Hafezi et al. |

(Continued)

FOREIGN PATENT DOCUMENTS

CN  101692258 A  4/2010

OTHER PUBLICATIONS

Moore, The Potential Use of Radio Frequency Identification Devices for Active Monitoring of Blood Glucose Levels, Journal of Diabetes Science and Technology, Jan. 2009; 3(1): 180-183; published online Jan. 2009; https://www.ncbi.nlm.nih.gov/pmc/articles/PMC2769845/, 6 pages.

(Continued)

*Primary Examiner* — Christian Jang
(74) *Attorney, Agent, or Firm* — Foley & Lardner LLP

(57) ABSTRACT

In one embodiment of the present disclosure, an ingestible medication device is a self-contained electronic device that stores an active agent, and that controls release of the active agent using an on board processor. The ingestible medication device embodies one or more ingestible device identifiers, including personal identifiers and active agent identifiers, which are compared with external device identifiers to determine whether to release the active agent. A method for managing an ingestible medication device detects proximity to a limited range, RFID-enabled patient wristband, indicating that the wristband is worn by the patient that ingested the ingestible medication device. Various methods enable a nurse to track medication information to monitor compliance with medication regimen and dosage information. Other methods track an ingestible medication device selected for filling a prescription at a pharmacy of the health care provider, including transfer to a caregiver station using a transport cart.

9 Claims, 10 Drawing Sheets

Related U.S. Application Data filed on Sep. 11, 2017, provisional application No. 62/556,997, filed on Sep. 11, 2017.

(51) Int. Cl.
| | |
|---|---|
| *A61B 5/07* | (2006.01) |
| *G16H 40/60* | (2018.01) |
| *H04L 67/12* | (2022.01) |
| *A61B 90/98* | (2016.01) |

(52) U.S. Cl.
CPC .............. *A61B 90/98* (2016.02); *G16H 40/60* (2018.01); *G16H 50/30* (2018.01); *H04L 67/12* (2013.01); *A61B 2560/0214* (2013.01); *A61B 2562/08* (2013.01)

(56) References Cited

U.S. PATENT DOCUMENTS

| | | | |
|---|---|---|---|
| 8,810,409 B2 | 8/2014 | Robertson et al. | |
| 8,847,766 B2 | 9/2014 | Zdeblick et al. | |
| 8,945,005 B2 | 2/2015 | Hafezi et al. | |
| 8,956,287 B2 | 2/2015 | Zdeblick et al. | |
| 9,361,657 B2 | 6/2016 | Hunt et al. | |
| 2002/0126036 A1* | 9/2002 | Flaherty | A61B 5/14532 |
| | | | 340/870.07 |
| 2003/0004424 A1* | 1/2003 | Birnbaum | A61B 5/6831 |
| | | | 600/520 |
| 2005/0147559 A1 | 7/2005 | Von Alten | |
| 2006/0047538 A1 | 3/2006 | Condurso et al. | |
| 2007/0055552 A1 | 3/2007 | St. Clair et al. | |
| 2008/0029532 A1 | 2/2008 | Handfield et al. | |
| 2010/0185055 A1 | 7/2010 | Robertson et al. | |
| 2010/0239616 A1 | 9/2010 | Hafezi et al. | |
| 2011/0009715 A1* | 1/2011 | O'Reilly | A61B 5/0022 |
| | | | 600/302 |
| 2011/0124983 A1* | 5/2011 | Kroll | A61B 90/90 |
| | | | 600/302 |
| 2012/0173576 A1* | 7/2012 | Gillam | G16H 10/60 |
| | | | 707/E17.014 |
| 2012/0293306 A1 | 11/2012 | Robertson et al. | |
| 2013/0126601 A1 | 5/2013 | Lee | |
| 2014/0163664 A1 | 6/2014 | Goldsmith | |
| 2014/0203950 A1 | 7/2014 | Zdeblick et al. | |
| 2015/0332283 A1 | 11/2015 | Witchey | |
| 2015/0343144 A1* | 12/2015 | Altschul | A61K 9/0097 |
| | | | 604/503 |
| 2016/0117471 A1 | 4/2016 | Belt et al. | |
| 2016/0183878 A1 | 6/2016 | Weast et al. | |
| 2016/0292672 A1* | 10/2016 | Fay | G06Q 20/363 |
| 2016/0310077 A1* | 10/2016 | Hunter | A61F 2/0059 |
| 2017/0132393 A1 | 5/2017 | Natarajan et al. | |
| 2017/0150939 A1* | 6/2017 | Shah | G16H 40/63 |

OTHER PUBLICATIONS

Proteus Digital Health press release, "U.S. FDA Accepts First Digital Medicine New Drug Application for Otsuka and Proteus Digital Health", <https://www.proteus.com/press-releases/u-s-fda-accepts-first-digital-medicine-new-drug-application-for-otsuka-and-proteus-digital-health/>, Sep. 10, 2015; 8 pages.

Doug Aamoth <http://techland.time.com/author/daamoth/>: "Motorola Is Working On a Password Pill for Once-Daily Authentication—Oh, and a Tattoo, Too", <http://techland.time.com/2013/05/31/motorola-is-working-on-a-password-pill-for-once-daily-authentication-oh-and-a-tattoo-too/>; May 31, 2013; 2 pages.

Andrea Cangialosi et al., "Leveraging RFID in Hospitals: Patient Life Cycle and Mobility Perspectives", IEEE Communications Magazine, vol. 45, issue 9; Sep. 2007; 6 pages.

Thomas Rades et al., Pharmaceutics—Drug Delivery and Targeting, "Controlling drug delivery", Chapter I, Pharmaceutical Press; published Oct. 16, 2009; 24 pages.

Jeff Shimizu et al., "Advanced Delivery Devices—IntelliCap: An Intelligent, Electronic Capsule for Oral Drug Delivery & Development", <http://drug-dev.com/advanced-delivery-devices-intellicap-an-intelligent-electronic-capsule-for-oral-drug-delivery-development/>, Drug Development and Delivery magazine; Apr. 2013; 11 pages.

Robert Belknap et al., "Feasibility of an Ingestible Sensor-Based System for Monitoring Adherence to Tuberculosis Therapy", <http://journals.plos.org/plosone/article?id=10.1371/journal.pone.0053373>, PLoS ONE 8(1): e53373; Oct. 26, 2016; 6 pages.

Steven Wong et al., "The digital pill Tracking medication adherence through electronic modalities", Med Technol. 2016;85(1):38-40., <http://www.uwomj.com/wp-content/uploads/2016/05/v85no1-13.pdf>, Spring 2016; 3 pages.

FDA News Release, "FDA approves pill with sensor that digitally tracks if patients have ingested their medication", <https://www.fda.gov/newsevents/newsroom/pressannouncements/ucm584933.htm>, Nov. 13, 2017; 3 pages.

Dr. Plyalea Pal, "TECHNOFILE Smart pill: Ingestible medical devices", ingeNiEous web magazine of NIE, <http://vnwr.nie.govintezine/azine2.5/bechnoflie.php>, Oct. 2014; 2 pages.

Mark Roberti," Smart Pills for Authentication—Tiny RFID transponders embedded in individual pills could help reduce counterfeiting of high-price drugs", <http://www.rfidjournal.com/articles/view?13860>, RFID Journal, Dec. 16, 2015; 2 pages.

Yanya Znamenskaya, "Three Ways Digital Technology can Transform the Pharmaceutical Industry", <https://patientstalk.net/2016/01/28/three-ways-digital-technology-can-transform-the-pharmaceutical-industry-2/>; Jan. 28, 2016;19 pages.

Andrew Grush, "Smart pills one step closer to reality, clinical trials to begin soon in the UK", <https://www.androidauthority.com/smart-pills-355702/>; Mar. 10, 2014; 5 pages.

Matthew Mientka , "New Smart Pill Remembers Your Passwords While Passing Through The Body", <http://www.medicaldaily.com/new-smart-pill-remembers-your-passwords-while-passing-through-body-247077>; Jun. 24, 2013; 11 pages.

Chris Davies, "Motorola developing digital tattoos and "smart pills" for next-gen wearables", <http://www.slashgear.com/motorola-developing-digital-tattoos-and-smart-pills-for-next-gen-wearables-30284209/>; May 30, 2013; 11 pages.

Sarah Aspler, "How ingestible sensors and smart pills will revolutionize healthcare", <https://www.marsdd.com/news-and-insights/ingestibles-smart-pills-revolutionize-healthcare/> ; Sep. 26, 2014; 6 pages.

Stanley Darma, "Smart Pill Contains Microchip to Monitor Patients' Medication"; <https://www.medgadget.com/2012/01/smart-pill-contains-microchip-to-monitor-patients-medication.html>; Jan. 18, 2012; 2 pages.

* cited by examiner

Ingestible Device Identifiers 200

Personal Identifier 210

Active Agent Identifier 220

External Device Identifiers 250

Wristband Identifiers 260
Mobile Reader Identifiers 270
Fixed Reader Identifiers 280
Blockchain Identifiers 290

FIG. 2

External Device Patient Identifiers 252

Wristband Patient Identifier 262
Mobile Reader Patent Identifier 272
Fixed Reader Patient Identifiers 282
Blockchain Patient Identifiers 292

External Device Medication Identifiers 254

Wristband Medication Identifiers 264
Mobile Reader Medication Identifiers 274
Fixed Reader Medication Identifiers 284
Blockchain Medication Identifiers 294

FIG. 3

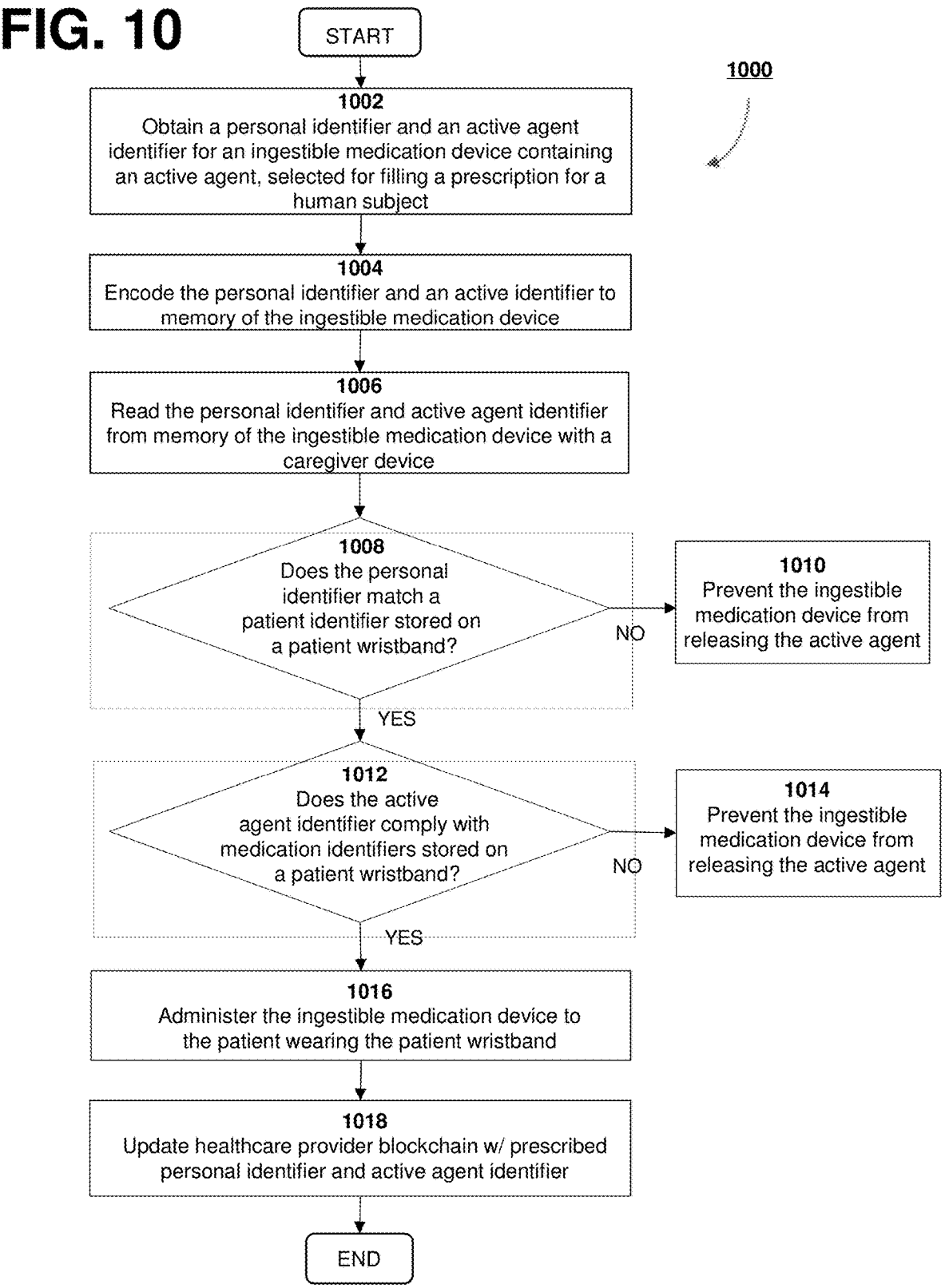

SYSTEM AND METHOD FOR INGESTIBLE DRUG DELIVERY

CROSS-REFERENCE TO RELATED APPLICATIONS

The present application claims benefit of U.S. Provisional App. No. 62/556,956, filed Sep. 11, 2017, claims the benefit of U.S. Provisional App. No. 62/556,978, filed Sep. 11, 2017, and claims the benefit of U.S. Provisional App. No. 62/556,997, filed Sep. 11, 2017, all of which are incorporated by reference in their entirety.

TECHNICAL FIELD

The present disclosure relates generally to a system and method for controlling drug delivery via an ingestible drug delivery device and, more particularly, to a system and method for tracking and administering ingestible drug delivery devices.

BACKGROUND

Medication errors (e.g., errors that occur in the ordering, dispensing, and administration of medications) are a significant consideration in the delivery of healthcare in an institutional setting, regardless of whether those errors cause injury. Various systems and methods are being developed at present to reduce the frequency of occurrence and severity of preventable adverse drug events and other medication errors. The administration of medication typically focuses on the following five factors: the right patient, the right drug, the right route, the right amount, and the right time.

In many healthcare facilities a bracelet device having the patient's identification, such as his or her name printed thereon, is affixed to a patient upon admittance to the facility in order to identify the patient during his or her entire stay. Despite this safeguard, opportunities arise for patient identification error. For example, when a blood sample is taken from a patient, the blood sample must be identified by manually transcribing the patient's name and other information from the patient's identification bracelet. In transferring the patient's name, a care-giver may miscopy the name or, instead of actually reading the patient's bracelet, rely on memory or a different data source which may be in error.

Several studies have documented that most medications in a hospital are given to the correct patient. However, the small percentage of medications that are given to the wrong patient is cause for great concern. This can happen if a patient is moved from one room to another and a new patient is now in the former patient's bed. Occasionally, the former patient's name may be left written on a board near the bed or by the doorway. While nurses are supposed to verify the patient's name or identification number written on a bracelet each time they administer a medication, this may not always happen. The nurse may receive a call to go to an emergency while giving a medication and thus be rushed, the patient may be unable to speak to identify themselves, or the nurse may not want to disturb a patient who is sleeping. Errors in giving medication to the wrong patient can cause a variety of reactions that can sometimes lead to death.

Additionally, errors can occur in verification and control of medication in an institutional setting. In some instances, prescription drugs are identified merely by a simple prescription slip, a slip of paper on which the patient's name and identification number have been hand-written by a care-giver who is to administer the treatment. In other cases, orders for prescription drugs are entered into an automated system, such as a computerized physician order entry ("CPOE") system. The prescription slip or the electronic prescription from the CPOE system is routed to the pharmacy, where the order is filled. Typically, pharmacies check the physician order against possible allergies of the patient and for possible drug interactions in the case where two or more drugs are prescribed, and also check for contraindications. Depending on the healthcare facility, the medication may be identified and gathered within the pharmacy and placed into a transport carrier or cart for transport to a nurse station. Once at the nurse station, the prescriptions are again checked against the medications that have been identified for delivery to ensure that no errors have occurred.

As the processing power of computers allow for greater computer functionality and the Internet technology era allows for interconnectivity between computing systems, many healthcare institutions store medical records electronically. However, since the implementation of these more sophisticated online tools, several shortcomings in these technologies have been identified. First, existing and conventional methods fail to provide fast and efficient analysis due to a high volume of healthcare information existing on different networks and computing infrastructures. Managing such information on different platforms is difficult due to number, size, content, or relationships of the data associated with the users. Second, information stored in a database may be susceptible to risk and/or fraudulent modification. Third, access to healthcare databases may be limited due to security concerns.

SUMMARY

The systems and methods described herein for ingestible drug delivery attempt to address various errors that can arise in the dispensing and administration of oral medications: ensuring that the right medication is administered to the right patient; avoiding errors in patient identification due to relocation of patients; avoiding over-dosing; and administering medications at the right time.

As described herein, an ingestible medication device can be a self-contained electronic device that stores an active agent designed to produce a physiological result in human beings and that controls release of the active agent using an on board processor. In an embodiment, the ingestible medication devices incorporates an active agent delivery module that triggers release of the active agent when it receives an authorization signal.

In an embodiment, the ingestible medication device communicates with one or more external device to control release of the active agent. In an embodiment, the ingestible medication device embodies one or more ingestible device identifiers. In an embodiment, the ingestible device identifiers include a personal identifier that associates an ingestible medication device with a given patient or other human subject. In certain embodiments, ingestible device identifiers include an active agent identifier, which includes data identifying an active agent contained in the ingestible medical device.

In an embodiment, one or more external devices include external device identifiers. In an embodiment, the external device identifiers may be compared with ingestible device identifiers to determine whether or not to authorize an ingestible medication device to release its active agent.

External device identifiers include, for example, external device patient identifiers and external device medication identifiers.

In an embodiment, electronic components of an ingestible medication device include onboard sensors, an electronics module, a power source, a microprocessor, memory, and a wireless communication module. In an embodiment, the ingestible medication device includes one or both of an RFID marker and an RFID reader. In an embodiment, an active agent delivery module incorporates a Micro-Electro-Mechanical System (MEMS) mechanism for release of the active agent.

In an embodiment, external devices include patient wristbands, caregiver handheld devices, and a healthcare provider computer system. In an embodiment, the healthcare provider computer system includes a blockchain database. In an embodiment, external devices include fixed RFID readers at various locations within a healthcare institution. In another embodiment, external devices include a patient sensor patch or other device worn on or embedded in the subject's body that may incorporate cardiac sensors or other biosensors.

In an embodiment, a method for managing an ingestible medication device detects proximity of an RFID-enabled wristband, or other external device, to a patient who has ingested an ingestible medication device. In an exemplary embodiment, an ingestible medication device detects an RFID-enabled patient wristband within a limited read range, indicating that the patient wristband is worn by the patient that ingested the ingestible medication device. In another embodiment, if the ingestible medication device detects another external device, such as fixed RFID reader, within its read range, that may indicate that the other external device is located in the room of the patient and/or near the bed of the patient. In some embodiments, external identifiers received from an external device within the read range of the ingestible medication device are compared with ingestible device identifiers to determine whether or not to release an active agent of the ingestible medication device to the human subject that ingested the device.

In various methods, a nurse or other caregiver administers one or more ingestible medication devices to a human subject, and tracks administered medication devices using a hand held caregiver device or an RFID-enabled patient wristband. These methods enable a nurse or other caregiver to track medication information such as active agent identifiers or other medication data stored in the administered ingestible medication devices. The caregiver can control the operation of an ingested medication device by confirming that the stored medication information complies with medication regimen and dosage information stored for the human subject in external devices of the healthcare provider institution as a prerequisite for releasing the active agent.

In various methods, a doctor, nurse or other healthcare professional uses a computerized ePrescription system and prescription fill processes to track prescribed medications including ingestible medication devices. In one embodiment, computerized prescription fill processes include cart-fill methods that rely upon RFID-enabled transport carriers or carts for transporting ingestible medication devices to a nurse station or other area of a health care facility. In various embodiments, prescribed ingestible medication devices are encoded with ingestible device identifier(s), which may include one or more of a personal identifier and an active agent identifier, among other possibilities.

In various methods, a doctor uses an ePrescription system to define a medication procedure. A medication procedure includes predetermined criteria under which a medication regimen and/or dosage may be modified or updated, typically based upon patient symptoms and/or side effects of medication; together with defined modifications or updates of the medication regimen and/or dosage upon occurrence of the predetermined criteria. In an embodiment, patient responses to caregiver queries based upon the medication procedure may cause the system to update medication regimen information for the patient based on a medication procedure. In another embodiment, patient medication requests may cause the system to update medication regimen information for the patient based on a medication procedure.

In an embodiment, a method comprises generating, by an ingestible medication device, an activation signal indicating ingestion of the ingestible medication device by a human subject, wherein the ingestible medication device contains an active agent designed to produce a physiological result in human beings; actuating, by a processor of the ingestible medication device, transmission of a limited range signal including an ingestible device identifier stored in the ingestible medication device; determining, by the processor of the ingestible medication device, whether the ingestible medication device has received an external device identifier from an external device in response to the receipt by the external device of limited range signal including the ingestible device identifier; in response to a determination that the ingestible medication device has received the external device identifier from the external device in response to the receipt by the external device of the ingestible device identifier, comparing, by the ingestible medication device, the ingestible device identifier with the external device identifier; and in response to a comparison of the ingestible device identifier with the external device identifier that indicates that the human subject is authorized to receive the active agent, releasing, by the ingestible medication device, the active agent to the human subject.

In an embodiment, a method for managing an ingestible medication device, comprises activating, by a power supply of an ingestible medication device, a processor of the ingestible medication device following ingestion of the ingestible medication device by a human subject, wherein the ingestible medication device contains an active agent designed to produce a physiological result in human beings and a carrier component for the active agent; transmitting, by the processor of the ingestible medication device, a limited range RFID signal including a personal identifier stored in an RFID marker of the ingestible medication device automatically upon the activating of the processor of the ingestible medication device; listening, by the processor of the ingestible medication device, for receipt by the ingestible medication device of a wristband patient identifier from a patient wristband including an RFID reader, in response to receipt by the patient wristband of the limited range RFID signal including the personal identifier; in response to a determination that the ingestible medication device has received the wristband patient identifier from the patient wristband in response to the receipt by the patient wristband of the ingestible device identifier, comparing, by the ingestible medication device, the personal identifier with the wristband patient identifier; and in response to a comparison of the personal identifier with the wristband patient identifier that indicates that the wristband patient identifier identifies the same human subject as the personal identifier, releasing, by the ingestible medication device, the active agent and the carrier component to the human subject.

In an embodiment, an ingestible medication device comprises a capsule body including an active agent dispensing module comprising a container for holding an active agent designed to produce a physiological result in human beings, and a carrier component for the active agent, the active agent dispensing module comprising a microactuator configured to release the active agent and the carrier component in response to receipt of an authorization signal; and an electronics module, coupled to the active agent dispensing module, the electronics module comprising a processor, a memory, and a power supply, the memory storing a personal identifier, wherein the processor in communication with the memory, the power supply and the active agent dispensing module, executes a set of instructions instructing the processor to: transmit a limited range RFID signal including the personal identifier stored in the memory; listen for receipt of a wristband patient identifier from a patient wristband including an RFID reader, in response to receipt by the patient wristband of the limited range RFID signal including the personal identifier; compare the personal identifier with the wristband patient identifier, upon receipt of the wristband patient identifier from the patient wristband in response to the receipt by the patient wristband of the personal identifier; and communicate the authorization signal to the active agent dispensing module, in the event the comparing the personal identifier with the wristband patient identifier indicates that the wristband patient identifier identifies the same human subject as the personal identifier; wherein, in the event of the communication by the processor of the authorization signal, the active agent dispensing module releases the active agent and the carrier component to the human subject.

In an embodiment, a method for tracking an ingestible medication device, comprises receiving, by a processor of a caregiver device, an activation signal following ingestion by a human subject of an ingestible medication device, wherein the ingestible medication device contains an active agent designed to produce a physiological result in human beings; interrogating, by a wireless communication module of a caregiver device in communication with the processor of the caregiver device, one of a processor of the ingestible medication device and a wristband device housed in a patient wristband worn by the human subject, to sense active agent identifiers stored in the one of the processor of the ingestible medication device and the wristband device contained in the patient wristband worn by the human subject, the active agent identifiers comprising dosage formulation information for the ingestible medication administered by the user of the caregiver device; storing, in a memory of the caregiver device in communication with the processor of the caregiver device, the active agent identifiers comprising dosage formulation information for the ingestible medication device; and communicating to a healthcare provider system, by the wireless communication module of the caregiver device, a request to update a patient record corresponding to the human subject, the patient record corresponding to a first blockchain stored on a plurality of network nodes of the healthcare provider system, the request instructing the healthcare provider system to append to the first blockchain a second blockchain including the active agent identifiers comprising the dosage formulation information for the ingestible medication device.

In an embodiment, a method for tracking an ingestible medication device comprises receiving, by an RFID device in communication with a processor of a patient wristband, an activation signal following ingestion by a human subject of an ingestible medication device, wherein the ingestible medication device contains an active agent designed to produce a physiological result in human beings; interrogating, by the RFID device of the patient wristband, a processor of the ingestible medication device to sense active agent identifiers stored in the processor of ingestible medication device, the active agent identifiers comprising dosage formulation information for the ingestible medication device; storing, by a memory in communication with the processor of the patient wristband, the active agent identifiers comprising dosage formulation information for the ingestible medication device; and communicating, by the RFID device of the patient wristband, the active agent identifiers comprising dosage formulation information for the ingestible medication device to a caregiver device in response to receipt by the RFID device of an interrogation signal from the caregiver device.

In an embodiment, an ingestible medication device comprises a capsule body including an active agent dispensing module comprising a container for holding an active agent designed to produce a physiological result in human beings, and a carrier component for the active agent, the active agent dispensing module comprising a microactuator configured to release the active agent and the carrier component in response to receipt of an authorization signal; and an electronics module, coupled to the active agent dispensing module, the electronics module comprising a processor, a memory, and a power supply ingestible medication device following ingestion of the ingestible medication device by a human subject, the memory storing active agent identifier comprising dosage formulation information for the ingestible medication device, wherein the processor in communication with the memory, the power supply and the active agent dispensing module, executes a set of instructions instructing the processor following activation by the power supply to transmit an RFID signal including the active agent identifier comprising dosage formulation information for the ingestible medication device stored in the memory; listen for receipt of a wristband medication identifier from a patient wristband including an RFID reader, in response to receipt by the patient wristband of the RFID signal including the active agent identifier comprising dosage formulation information for the ingestible medication device, wherein the wristband medication identifier comprises medication regimen and dose information for the human subject; compare the active agent identifier with the wristband medication identifier, upon receipt of the wristband medication identifier from the patient wristband including the RFID reader; and communicate the authorization signal to the active agent dispensing module, in the event the comparing the active agent identifier with the wristband medication identifier indicates that the active agent identifier comprising dosage formulation information for the ingestible medication device complies with the medication regimen and dose information for the human subject of the wristband medication identifier; wherein, in the event of the communication by the processor of the authorization signal, the active agent dispensing module releases the active agent and the carrier component to the human subject.

In an embodiment, a method for tracking an ingestible medication device comprises obtaining, by a processor, an ingestible device identifier for an ingestible medical device selected for filling a prescription for a human subject at a healthcare institution, wherein the ingestible medication device contains an active agent designed to produce a physiological result in human beings, and wherein the ingestible medication device contains a memory in communication with a processor that selectively activates release of the active agent from the ingestible medical device following ingestion of the ingestible medical device; encoding, by the processor, the ingestible device identifier to the memory in communication with the processor of the ingestible medical device selected for filling a prescription for a human subject; and generating, by the processor, a request to update a patient record corresponding to the human subject, the patient record corresponding to a first blockchain stored on a plurality of network nodes of a system of the healthcare institution, the request instructing the provider system to append to the first blockchain a second blockchain including a transaction of encoding the ingestible device identifier to the memory of the ingestible medication device.

In an embodiment, a method for tracking an ingestible medication device, comprises obtaining, by a processor, an ingestible device identifier for an ingestible medical device selected for filling a prescription for a human subject at a pharmacy, wherein the selected ingestible medication device contains an active agent designed to produce a physiological result in human beings, and wherein the selected ingestible medication device contains a memory in communication with a processor that selectively activates release of the active agent from the ingestible medical device following ingestion of the ingestible medical device; encoding, by a wireless communication module of a transport carrier device, the ingestible device identifier to the memory of the ingestible medical device selected for filling a prescription for a human subject, wherein the transport carrier device is configured to transport medications of filled prescriptions from the pharmacy to a caregiver station; and reading, by a processor of a device at the caregiver station, the ingestible device identifier of the ingestible medical device from one of the transport carrier device and the ingestible medical device.

In an embodiment, an ingestible medication device comprises a capsule body including an active agent dispensing module comprising a container for holding an active agent designed to produce a physiological result in human beings, and a carrier component for the active agent, the active agent dispensing module comprising a microactuator configured in response to receipt of an authorization signal to release the active agent and the carrier component; and an electronics module, coupled to the active agent dispensing module, the electronics module comprising a processor, a memory, and a power supply, the memory being configured to be programmed with one or more ingestible device identifier following manufacture, wherein the processor in communication with the memory, the power supply and the active agent dispensing module, executes a set of instructions instructing the processor to: receive an external device identifier from an external device via wireless communication with the ingestible medical device; compare the programmed one or more ingestible device identifier with the external device identifier; and communicate the authorization signal to the active agent dispensing module, in the event the comparing the one or more ingestible device identifier with the external device identifier indicates that human subject is authorized to receive the active agent; wherein, in the event of the communication by the processor of the authorization signal, the active agent dispensing module releases the active agent and the carrier component to the human subject.

Other objects, features, and advantages of the present disclosure will become apparent with reference to the drawings and detailed description of the illustrative embodiments that follow.

BRIEF DESCRIPTION OF THE DRAWINGS

Non-limiting embodiments of the present disclosure are described by way of example with reference to the accompanying figures which are schematic and are not intended to be drawn to scale. Unless indicated as representing the background art, the figures represent aspects of the disclosure.

FIG. 2 is a block schematic diagram of ingestible device identifiers and external device identifiers stored by an ingestible drug delivery device and external healthcare devices, according to an embodiment.

FIG. 3 is a block schematic diagram of patient identifiers and medication identifiers stored by external healthcare devices, according to an embodiment.

FIG. 10 is a flow chart schematic diagram of a method for tracking and administering an ingestible drug delivery device selected in filling a prescription, according to an embodiment.

DETAILED DESCRIPTION

In the following detailed description, reference is made to the accompanying drawings, which depict non-limiting, illustrative embodiments of the present disclosure. Other embodiments may be utilized and logical variations, e.g., structural and/or mechanical, may be implemented without departing from the scope of the present disclosure. To avoid unnecessary detail, certain information, items, or details known to those skilled in the art may be omitted from the following description.

Ingestible Medication Device and Wireless Network

Figure 1:
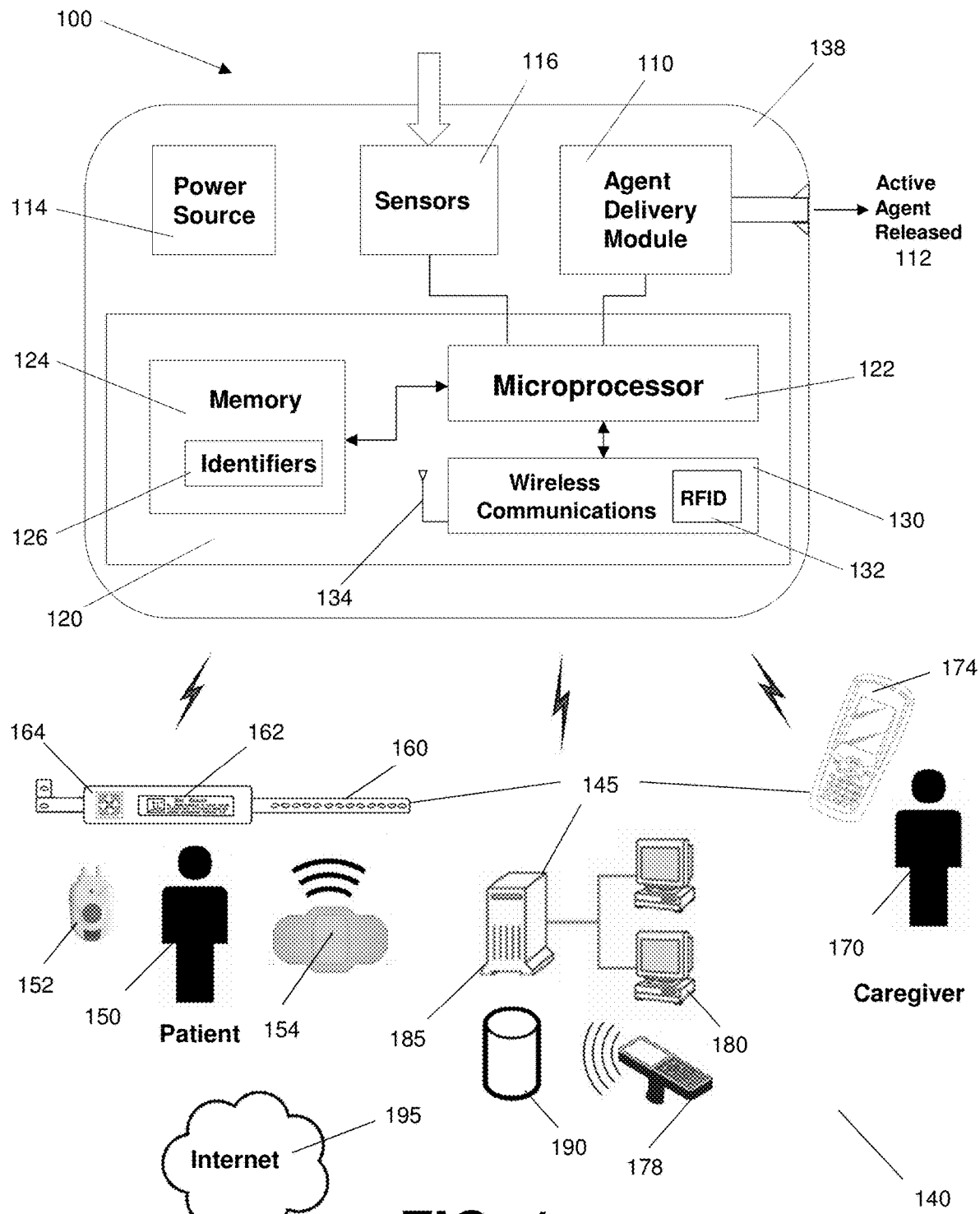
FIG. 1 is a system architecture for an ingestible drug delivery device and a network of a healthcare provider institution for tracking and managing administration of the ingestible drug delivery device, according to an embodiment.

As shown in FIG. 1, an ingestible medication device 110 (also herein called ingestible drug delivery device, or smart pill) is a self-contained electronic device comprising onboard sensors 116, an active agent delivery module (e.g., a MEMS drug delivery system) 110, an electronics module 120, and a power source (e.g., battery) 114. The electronics module 120 comprises a microprocessor (e.g., a micro controller) 122, memory (e.g., flash memory, one-time programmable memory, etc.) 124, and wireless communication module 130 (e.g., a transponder having an antenna 134). Among other contents, the memory may store one or more identifiers 126 of the ingestible medication device 100. Identifiers 126 also may be stored in other modules of ingestible medication device 100.

In an embodiment, the ingestible medication device 100 is implemented on a printed flex circuit 138 in which the antenna 134 is embedded. In one form factor, flex circuit 138 is then rolled and formed into a capsule configuration. The smart pill 100 can also be implemented as a system-in-package (SiP) that can take several configurations (e.g., a rolled printed flex board).

In the present systems and methods, the ingestible medication device can communicate with various external devices 145 within a wireless network 140 of the healthcare provider. External devices 145 may generate, receive, and/or communicate data, e.g., physiological data of a patient 150. These wireless communications may include closed communications at a healthcare provider institution (e.g., hospital, hospice, or resident care center) as well as communications transmitted over the internet 195. Various external devices 145 of the patient and of the healthcare provider (e.g., nurse or other caregiver 170, physician, pharmacist) may communicate with the ingestible drug delivery device 100 to carry out the methods and systems of the present disclosure, as discussed below.

Active Agent/Carrier Component

The ingestible medication delivery device 100 includes an active agent/carrier component. In an embodiment, the active agent/carrier component includes a composition, which may be a solid or fluid (e.g., liquid), which has an amount of active agent, e.g., a dosage, present in a pharmaceutically acceptable carrier. The active agent together with the carrier component are sometimes referred to herein as a "dosage formulation".

The active agent (also herein called drug) includes any compound or mixture of compounds which produces a physiological result, e.g., a beneficial or useful result, upon contact with a human being (also herein called a patient or a subject). Active agents are distinguishable from such components as vehicles, carriers, diluents, lubricants, binders and other formulating aids, and encapsulating or otherwise protective components. The active agent may be any molecule, as well as binding portion or fragment thereof, that is capable of modulating a biological process in a living subject. In certain embodiments, the active agent may be a substance used in the diagnosis, treatment, or prevention of a disease or as a component of a medication. In certain embodiments, the active agent may be a chemical substance, such as a narcotic or hallucinogen, which affects the central nervous system and causes changes in behavior.

The active agent (i.e., drug) is capable of interacting with a target in a living subject. The target may be a number of different types of naturally occurring structures, where targets of interest include both intracellular and extracellular targets. Such targets may be proteins, phospholipids, nucleic acids and the like, where proteins are of particular interest. Specific proteinaceous targets of interest include, without limitation, enzymes, e.g., kinases, phosphatases, reductases, cyclooxygenases, proteases and the like, targets comprising domains involved in protein-protein interactions, such as the SH2, SH3, PTB and PDZ domains, structural proteins, e.g., actin, tubulin, etc., membrane receptors, immunoglobulins, e.g., IgE, cell adhesion receptors, such as integrins, etc., ion channels, transmembrane pumps, transcription factors, signaling proteins, and the like.

The active agent may include one or more functional groups necessary for structural interaction with the target, e.g., groups necessary for hydrophobic, hydrophilic, electrostatic or even covalent interactions, depending on the particular drug and its intended target. Where the target is a protein, the drug moiety may include functional groups necessary for structural interaction with proteins, such as hydrogen bonding, hydrophobic-hydrophobic interactions, electrostatic interactions, etc., and may include at least an amine, amide, sulfhydryl, carbonyl, hydroxyl or carboxyl group, such as at least two of the functional chemical groups.

Drugs of interest may include cyclical carbon or heterocyclic structures and/or aromatic or polyaromatic structures substituted with one or more of the above functional groups. Also of interest as drug moieties are structures found among biomolecules, including peptides, saccharides, fatty acids, steroids, purines, pyrimidines, derivatives, structural analogs or combinations thereof. Such compounds may be screened to identify those of interest, where a variety of different screening protocols are known in the art.

The drugs may be derived from a naturally occurring or synthetic compound that may be obtained from a wide variety of sources, including libraries of synthetic or natural compounds. For example, numerous means are available for random and directed synthesis of a wide variety of organic compounds and biomolecules, including the preparation of randomized oligonucleotides and oligopeptides. Alternatively, libraries of natural compounds in the form of bacterial, fungal, plant and animal extracts are available or readily produced. Additionally, natural or synthetically produced libraries and compounds are readily modified through conventional chemical, physical and biochemical means, and may be used to produce combinatorial libraries. Known pharmacological agents may be subjected to directed or random chemical modifications, such as acylation, alkylation, esterification, amidification, etc. to produce structural analogs.

The ingestible drug delivery device may further include a pharmaceutically acceptable vehicle for the active agent (i.e., carrier). As used herein, the phrase "pharmaceutically acceptable" means approved by a regulatory agency of the federal or a state government, or listed in the U.S. Pharmacopeia, European Pharmacopeia, or other generally recognized pharmacopeia for use in humans. Common carriers and excipients, such as corn starch or gelatin, lactose, dextrose, sucrose, microcrystalline cellulose, kaolin, mannitol, dicalcium phosphate, sodium chloride, and alginic acid are of interest. Disintegrators commonly used in the formulations of the invention include croscarmellose, microcrystalline cellulose, corn starch, sodium starch glycolate and alginic acid.

The ingestible drug delivery device can be configured for the delivery of liquid, semi-liquid or solid forms of drug, or all three. Solid forms of drug can include both powder or pellet. Semi liquid can include a slurry or paste. The drug can be contained within a cavity of the capsule, or in the case of the liquid or semi-liquid, within an enclosed reservoir. In some embodiments, the capsule can include a first, second, or a third drug (or more). Such drugs can be contained within the tissue penetrating member lumen (in the case of solids or powder) or in separate reservoirs within the capsule body. The active agent may be in a powder, liquid, and/or gel.

A liquid composition may comprise a suspension or solution of the compound or pharmaceutically acceptable salt in a suitable liquid carrier(s), for example, ethanol, glycerin, sorbitol, non-aqueous solvent such as polyethylene glycol, oils or water, with a suspending agent, preservative, surfactant, wetting agent, flavoring or coloring agent. Alternatively, a liquid formulation can be prepared from a reconstitutable powder. For example, a powder containing active compound, suspending agent, sucrose and a sweetener can be reconstituted with water to form a suspension; and a syrup can be prepared from a powder containing active ingredient, sucrose and a sweetener.

A composition in the form of a tablet or pill can be prepared using any suitable pharmaceutical carrier(s) routinely used for preparing solid compositions. Examples of such carriers include magnesium stearate, starch, lactose, sucrose, microcrystalline cellulose and binders, for example, polyvinylpyrrolidone. The tablet can also be provided with a color film coating, or color included as part of the carrier(s). In addition, the active agent can be formulated in a controlled release dosage form as a tablet comprising a hydrophilic or hydrophobic matrix.

In the present system and method for ingestible drug delivery, one function of the carrier can be as part of a mechanism for controlled release of the active agent.

Agent Delivery Module

In an embodiment, the ingestible drug delivery device includes an agent delivery module 110 that controls release of the active agent. In an embodiment, the agent delivery module has a normally-inactive state and the agent delivery module must receive authorization data in order to release the active agent 112. The release of active agent can be through a variety of mechanisms; osmotic plug piston, polymer cracking or trigger initiated solubilization on the capsule itself or other capsule voids, release from ion-bound linkage from polymer side chains to release the active agent. In an embodiment, the agent delivery module 110 incorporates a Micro-Electro-Mechanical System (MEMS) mechanism for release of the active agent.

In another embodiment, the smart pill 100 includes a dissolving component that neutralizes/blocks the active agent. The smart pill can also be obtained by sealing a passage to the dissolving component, neutralizing the active part by "cementing" it in an inert material to neutralize the active agent chemically or physically (via temperature/light etc.).

In another mode, the agent delivery module 100 has a normally-active state and the ingestible drug delivery device includes a deactivation module that includes a deactivator substance or mechanism that causes the active agent to deactivate. In this embodiment, the deactivation module (not shown) is operatively coupled to the agent delivery module 110. In one embodiment, the deactivation module comprises a container for holding a volume and/or quantity of a deactivator substance and a microactuator for dispensing the deactivator to the agent delivery module.

In an embodiment, in the event agent delivery module 110 is not activated to release the active agent, or is prevented from releasing the active agent, the ingestible medication device 100 will not release the active agent into the system of patient 150 and instead the active agent together with its carrier component will travel through the body and be evacuated in the patient's feces.

Electronics Module

The electronics module 120 can be configured to receive at least one signal from the one or more sensors and to provide instructions in the form of at least one signal to the one or more active agent module(s) and/or deactivation module(s). The digital processing units can be configured to receive at least one signal from the one or more sensors and to process the signal into one or more resulting instructions and provide the instructions in the form of at least one signal to the programmable microprocessor.

The electronics module includes a wireless communications module 130 (also herein called wireless communication interface) that provides both transmit and receive communication and is configured to receive at least one signal from the one or more digital processing units, for example other devices associated with the patient 150, devices 145 external to the patient, and other ingestible drug delivery devices 100 that have been administered to the patient. In an embodiment, one or more device(s) in communication with ingestible medication device 100 provide information in the form of at least one signal that determine whether or not the agent delivery module 110 releases the active agent 112. A signal can include, for example, an optic signal, a light signal, a chromatic signal, an acoustic signal, a vibrational signal, an infrared (IR) signal, an electronic signal, a digital signal, a radio signal, a wireless signal, or any other detectable signal. A signal from the one or more sensors, digital processing unit, or programmable microprocessor can be part of the communication between the one or more sensors, the programmable microprocessor, the digital processing unit, and/or the one or more agent delivery module 110.

A signal generation component of the communication interface 130 may include a distinct transmitter component that serves to transmit the generated signal to a remote receiver. The receiver may be included in a device closely associated with the patient, e.g., worn on or embedded in the patient's body (e.g., sensor patch 154; wrist band 160). Additionally, the receiver may be remote from the patient (e.g., mobile device 174 carried by a nurse or other caregiver 170; computer terminals 180 of the healthcare provider institution). The transmitter component, when present, may take a number of different configurations, e.g., depending on the type of signal that is generated and is to be emitted. In certain embodiments, the transmitter component is made up of one or more electrodes. In certain embodiments, the transmitter component is made up of one or more wires, e.g., in the form of antenna(e). In certain embodiments, the transmitter component is made up of one or more coils. As such, the signal transmitter may include a variety of different transmitters, e.g., electrodes, antennas (e.g., in the form of wires) coils, etc. In certain embodiments, the signal is transmitted either by one or two electrodes or by one or two wires. A two-electrode transmitter is a dipole; a one electrode transmitter forms a monopole.

Vehicles of communication include healthcare provider network 140. In various aspects, the healthcare provider network 140 may comprise local area network(s) (LAN) as well as wide area network(s) (WAN) including without limitation Internet 195, wired channels, wireless channels, communication devices including telephones, computers, wire, radio, optical or other electromagnetic channels, and combinations thereof, including other devices and/or components capable of/associated with communicating data. For example, the communication environments include in-body communications, various devices, various modes of communications such as wireless communications, wired communications, and combinations of the same. In various embodiments as described below, the healthcare network 140 embodies blockchain technology for distributed storage of healthcare information.

Wireless communication modes include any mode of communication between points that utilizes, at least in part, wireless technology including various protocols and combinations of protocols associated with wireless transmission, data, and devices. The points include, for example, wireless devices such as wireless headsets, audio and multimedia devices and equipment, such as audio players and multimedia players, telephones, including mobile telephones and cordless telephones, and computers and computer-related devices and components, such as printers.

Accordingly, in various aspects, the communications interface 130 may comprise one or more interfaces such as, for example, a wireless communications interface, a network interface, a transmit interface, a receive interface, a media interface, a system interface, a component interface, a switching interface, a chip interface, a microprocessor, and so forth. When implemented by a wireless device or within wireless system, for example, the mobile computer may include a wireless interface comprising one or more antennas, transmitters, receivers, transceivers, amplifiers, filters, control logic, etc.

In various implementations, the described aspects may communicate over wireless shared media in accordance with a number of wireless protocols. Examples of wireless protocols may include various wireless local area network (WLAN) protocols, including the Institute of Electrical and Electronics Engineers (IEEE) 802.xx series of protocols, such as IEEE 802.11a/b/g/n, IEEE 802.16, IEEE 802.20, etc. Other examples of wireless protocols may include various wireless wide area network (WWAN) protocols, such as GSM cellular radiotelephone system protocols with GPRS, CDMA cellular radiotelephone communication systems with 1xRTT, EDGE systems, EV-DO systems, EV-DV systems, HSDPA systems, and so forth. Further examples of wireless protocols may include wireless personal area network (PAN) protocols, such as an Infrared protocol, a protocol from the Bluetooth Special Interest Group (SIG) series of protocols, including Bluetooth Specification versions v1.0, v1.1, v1.2, v2.0, v2.0 with Enhanced Data Rate (EDR), as well as one or more Bluetooth Profiles, and so forth. Yet another example of wireless protocols may include near-field communication techniques and protocols, such as electro-magnetic induction (EMI) techniques. An example of EMI techniques may include passive or active radio-frequency identification (RFID) protocols and devices. Other suitable protocols may include Ultra Wide Band (UWB), Digital Office (DO), Digital Home, Trusted Platform Module (TPM), ZigBee, etc.

In an embodiment, communications interface 130 includes a radio frequency identification (RFID) tag configured to transmit signals that can be read by an RFID reader included in patient wristband 160. In other embodiments, communications interface 130 includes an RFID tag 132 (also herein called RFID marker 132) configured to transmit signals that can be read by a fixed RFID reader 178 associated with the healthcare provider network 140. RFID marker 132 also may be housed in other modules of ingestible medication device 100. In an embodiment, the healthcare provider network 140 includes a plurality of fixed RFID readers respectively associated within given rooms, and/or respectively proximate to given beds, within the healthcare provider institution. In a further embodiment, communications interface 130 includes an RFID tag configured to transmit signals that can be read by an RFID reader or scanner included in a mobile electronic device 174 carried by a caregiver 170, when the caregiver 170 is near patient 150.

In these embodiments, the RFID marker 132 within communications interface 130 may be an active tag, which includes a power source for transmission of RFID signals. In an embodiment, the active RFID tag may use the power source 114. In other embodiments, the RFID marker 132 within communications interface 130 may be a passive RFID tag, which obtains powers from the signal of an external reader in order to transmit an RFID signal.

In various embodiments, communications interface 130 includes an RFID reader that detects and identifies signals transmitted by patient wristband 160. Communications interface 130 may include an RFID reader that detects and identifies signals transmitted by a fixed RFID reader 178 associated with the healthcare provider network 140. In an embodiment, the healthcare provider network 140 includes a plurality of fixed RFID readers 178 respectively associated within given rooms, and/or proximate to given beds, within the healthcare provider institution. In an embodiment, fixed RFID reader 178 reads data from an RFID tag 164 of patient wristband 160, and transmits this data to an RFID reader within communications module 130. In a further embodiment, a caregiver 170 uses an RFID reader or scanner included in a mobile electronic device 174 to detect data from an RFID tag 164 of patient wristband 160, and mobile electronic device 174 transmits this data to communications module 130 of ingestible medication device 100.

Another embodiment of mobile device 174 is a transport carrier for transporting medications dispensed in filling prescriptions from a pharmacy of the healthcare institution to a nurse station or other site. In an embodiment, the transport carrier 174 is RFID-enabled to read and encode RFID markers 132 in ingestible medication devices 100.

In various embodiments, RFID communications between the communications interface 130 of ingestible medication device 100 and other devices, such as patient wristband 160, employ communications at UHF frequencies using passive tag technology. In passive RFID systems, an RFID reader and reader antenna send a radio signal to the tag. The RFID tag uses the transmitted signal to power on, and reflect energy back to the reader. Passive UHF systems can have read ranges as long as 12 m, or may have shorter ranges depending on the type of passive UHF system. In an embodiment, RFID communications in the UHF frequency band are regulated by the ECPglobal Gen2 (ISO 18000-6C) UHF global standard. In an embodiment, these UHF RFID communication use the 902-928 MHz band in North America, and use the 865-868 MHz band in Europe.

In an embodiment, the communications interface 130 of ingestible medication device sends and/or receives a limited range signal from one or more external device 145. In one embodiment, the limited-range signal is an RFID signal in the UHF frequency band. For example, a patient wristband 160 worn by patient 150 may receive a limited-range signal from an ingestible medication device that has been ingested by the patient, whereas a patient wristband in a different room of the healthcare institution would not receive the limited range signal. In one embodiment, the limited range signal has a range no greater than 3 m. In another embodiment, the limited range signal has a range no greater than 2 m. In a further embodiment, the limited range signal has a range no greater than 1 m. Successful transmission or receipt of the limited range signal indicates proximity of the patient 150 (and any ingestible medication device 100 ingested by the patient) to the external device 145, and may be used in various methods for management of ingestible medication devices 100 based upon localization of patients 150 and/or external devices 145. In the event of failure successfully to transmit the limited range signal from ingestible medication device 100 to an external device such as an RFID wristband 160, or from the RFID wristband 160 to the ingestible medication device 100, this failure may indicate that the RFID is out-of-range from the ingestible medication device 100. In this case, after failure to receive a signal (e.g., within a predetermined period of time), the ingestible medication device 100 or RFID wristband 160 can send an out-of-range notification, e.g., to the healthcare provider server 185.

In an embodiment, healthcare provider network 140 includes a wired or wireless nurse call device 152, e.g., located on or adjacent the hospital bed, for patients 150 to alert a nurse or other caregiver 170 of their need for help.

The communication interface 130 can be configured with one or more transmitter and/or one or more receiver for communication transmissions such as radio waves to control communications that includes data from one or more sensor 116. For example, the one or more sensor 116 may include a capability of transmitting radio frequency signals. These radio frequency signals may include, e.g., an analyte sensor-enabled RFID tag, such described in Moore, J. Diabetes Sci. Technol. 3: 180-183, 2009, which is incorporated by reference in its entirety. In another embodiment, miniaturized (0.5×0.5×5 mm) implantable sensors are an implantable sensor that senses glucose levels and transmits the information to a proximal communicator.

A bio-sensor chip can be used that includes a passive transponder, glucose sensor and integrated circuitry. See, e.g., U.S. Pat. No. 7,125,382 to Zhou entitled "Embedded Bio-sensor System," which is incorporated herein by reference in its entirety. Transmission communications may include frequency-hopping spread spectrum technology such as BLUETOOTH® wireless technology.

Power source 114 within ingestible medical device 100 may be a battery or other power source. In some embodiments, the power source includes an activation component that is activated following ingestion of the smart pill. The activation component is a component that activates the power source upon experience of a stimulus, e.g., contact of the composition with a target physiological site of interest, such as the stomach. The activation component may be configured to be activated in a number of different ways. Illustrative activation approaches include, but are not limited to: battery completion, e.g., battery activated by electrolyte addition, and battery activated by cathode or anode addition; battery connection, e.g., battery activated by conductor addition; among others.

In the case of battery activation by electrolyte addition, the battery includes, when completed, a cathode, an anode, and an electrolyte. When the ingestible drug delivery device (e.g., smart pill) is ingested and travels through the esophagus, it eventually enters the stomach. The cathode and anode provided within the composition do not constitute a full battery. However, as the composition dissolves to expose the cathode and anode, the stomach fluid acts as the electrolyte component of the battery. The added component of the stomach fluid thus completes the battery. Therefore, as the composition contacts the target site, e.g., by entering the stomach and dissolving to the point of cathode and anode exposure, a power source is provided which activates the identifier, e.g., in chip configuration.

Another activation approach involves a battery activated by cathode or anode addition. In this approach, the power supply is activated by having the triggering event add a cathode or anode component, with the electrolyte being intrinsic in the partial, pre-battery configuration. The battery is completed, producing power and activating the composition, although not necessarily at the identical point of time.

In another embodiment, the power supply includes a battery that is activated by conductor addition. In this approach, the power supply comprises a battery that is connected to the circuitry when it enters the stomach. The battery becomes connected by conductor addition. In this case, there is a physically complete battery and a complete chip. When these two components are awash in physiological fluid, such as in the stomach, they become electronically connected.

In certain embodiments, the power source 114 includes a power storage element. For example, a duty cycle configuration may be employed, e.g., where slow energy production from a battery is stored in a power storage element, e.g., in a capacitor, which then provides a burst of power that is deployed to the signal generation component. In certain embodiments, the power supply includes a timing element which modulates, e.g., delays, delivery of power.

In certain embodiments, the system further includes a memory 124, i.e., element for storing data. Typically, the memory is a computer readable medium. The term "computer readable medium" as used herein refers to any storage or transmission medium that participates in providing instructions and/or data to a computer for execution and/or processing. Examples of storage media include floppy disks, magnetic tape, CD-ROM, a hard disk drive, a ROM or integrated circuit, a magneto-optical disk, or a computer readable card such as a PCMCIA card and the like, whether or not such devices are internal or external to the computer. A file containing information may be "stored" on computer readable medium, where "storing" means recording information such that it is accessible and retrievable at a later date by a computer. With respect to computer readable media, "permanent memory" refers to memory that is permanent. Permanent memory is not erased by termination of the electrical supply to a computer or processor. Computer hard-drive ROM (i.e., ROM not used as virtual memory), CD-ROM, floppy disk and DVD are all examples of permanent memory. Random Access Memory (RAM) is an example of non-permanent memory. A file in permanent memory may be editable and re-writable.

The invention also provides computer executable instructions (i.e., programming) for performing the methods of the present disclosure. The computer executable instructions are present on a computer readable medium. Accordingly, various embodiments provide a computer readable medium containing programming for use in detecting and processing a signal generated or received by the ingestible drug delivery device of the present disclosure.

Ingestible Device Identifiers and External Device Identifiers

Also present in the ingestible medication device is one or more identifier 126, also herein called ingestible device identifiers 200 (FIG. 2).

In certain embodiments, an ingestible device identifier 200 is a component that emits a signal upon activation by a stimulus, e.g., by interrogation, upon contact with a target physiological location, etc. As such, the identifier may be an identifier that emits a signal when it contacts a target body (i.e., physiological) site. In addition, or alternatively, the identifier may be an identifier that emits a signal when interrogated. The identifier may be any component or device that is capable of generating a detectable signal following activation in response to a stimulus. In certain embodiments, the stimulus activates the identifier to emit a signal once the composition comes into contact with a physiological target site. For example, a patient may ingest a pill that upon contact with the stomach fluids, generates a detectable signal. Depending on the embodiment, the target physiological site or location may vary, where representative target physiological sites of interest include, but are not limited to, a location in the gastrointestinal tract, such as the mouth, esophagus, stomach, small intestine, large intestine, etc.

In some embodiments, when a stimulus activates the ingestible device identifier 200, the identifier emits a signal that is then received and processed, e.g., to compare the ingestible device identifier 200 with external device identifier(s) stored by one or more external device 145. In other embodiments, when the power source 114 is activated, the ingestible medical device emits an activation signal indicating the ingestion of an ingestible medication device 100, and an external device then transmits an interrogation signal to the ingestible medication device 100. For example, the ingestible medical device may contain a passive RFID tag, and when the ingestible medical device emits the activation signal that is detected by an external RFID reader, the reader then interrogates the passive RFID tag.

In an embodiment, the ingestible device identifiers 200 include a personal identifier 210 associating a given ingestible medication device with a given patient 150 or other subject. This identifier can associate the ingestible medication device with a personal identification number for a given patient, such as an official number used for tracking individuals like a social security number or driver's license number, or a patient identification number that can be assigned by a healthcare provider institution to a patient upon admission, among other possibilities.

Personal identifier 210 may also include other identifying information unique to a patient 150. For example, the personal identifier may include unique bio-electric signals or other biometric identifiers. In an embodiment, personal identifier 210 may include personal electrical signals of patient 150, as described below.

In certain embodiments, ingestible device identifiers 200 include active agent identifier(s) 220, i.e., data identifying an active agent, stored in active agent delivery module 110 or otherwise contained in the ingestible medical device 100. In an embodiment, an active agent identifier 220 identifies a particular active agent selected from a group or plurality of different active agents. In certain embodiments the active agent identifier 220 may, when associated with a batch of unit dosages, e.g., a batch of tablets, be indistinguishable from an active agent identifier 220 for any other unit dosage member of the batch.

In yet other embodiments, the active agent identifier 220 uniquely identifies a given unit dosage, even from other identical unit dosages in a given batch. In certain embodiments the active agent identifier 220 emits a unique signal that distinguishes a given type of unit dosage from other types of unit dosages, e.g., a given medication from other types of medications. In certain embodiments, the active agent identifier 220 emits a unique signal that distinguishes a given unit dosage from other unit dosages of a defined population of unit dosages, e.g., a prescription, a batch or a lifetime production run of dosage formulations.

In certain embodiments, the active agent identifier 220 comprises an identification code, such as a serial number assigned during production, that uniquely identifies a particular ingestible medication device 100 from all other ingestible medication devices.

In various embodiments, methods of the present disclosure compare one or more ingestible device identifier(s) 200 stored in ingestible medical device 100 with one or more external device identifiers 250 to determine whether to cause the active agent delivery module 100 to release an active agent. This comparison may be carried out by ingestible medical device 100, or by one or more external device 145. With further reference to FIG. 2, ingestible device identifier(s) 200 may be compared with one or more of the following external device identifiers 250, stored on one or more of external devices 145. Examples of external device identifiers 250 include wristband identifier(s) 260 stored on wristband label 160, e.g., sensed by an RFID reader within ingestible medical device 100; mobile reader identifier(s) 270 stored on a caregiver's mobile device 174, e.g., sensed by an RFID scanner included in device 174; fixed reader identifier(s) 280 stored on a fixed RFID reader 278; and blockchain identifiers 290 stored in healthcare provider distributed database (blockchain) 190 which may be compared with personal identifier 210 using a correlation engine of server 185.

Communication of ingestible device identifier(s) 200 stored in ingestible medical device 100 to external devices 145 can involve a series of data communications involving multiple external devices 145. For example, ingestible medical device 100 can transmit medication dosage information to a patient wristband (wristband medication identifier 264), and a handheld caregiver device 174 can then read wristband medication identifier 264 stored on wristband label 160. In turn, the handheld caregiver device 174 can transmit the medication dosage information to be posted to the healthcare provider distributed database (blockchain) 190.

In various embodiments, in determining whether to cause the active agent delivery module 110 to release an active agent, the present systems and methods compare one or more personal identifier 210 stored in ingestible medical device 100 with one or more patient identifier 252 stored in an external device 145. Examples of patient identifier(s) 252 stored on external devices 145 (FIG. 3) include wristband patient identifier 262 stored on wristband label 160; a mobile reader patient identifier 272 on a caregiver's mobile device 174; a fixed reader patient identifier 282 stored on a fixed RFID reader 178; and a blockchain patient identifier 292 stored in healthcare provider distributed database (blockchain) 190.

In various embodiments, in comparing the ingestible device identifier 200 with external device identifiers 250 from an external device to determine whether to cause the active agent delivery module 110 to release an active agent, the ingestible medical device 100 or external device 145 applies one or more additional criterion before authorizing release of the active agent. For example, as an additional criterion, ingestible medical device 100 and/or external device 145 compares one or more active agent identifier(s) 220 stored in ingestible medical device 100 with medication identifier(s) stored on one or more of external devices 145. Examples of medication identifier(s) 254 stored on external devices 145 (FIG. 3) include wristband medication identifier 264 stored on wristband label 160; a mobile reader medication identifier 274 on a caregiver's mobile device 174; a fixed reader medication identifier 284 stored on a fixed RFID reader 178; and a blockchain identifier 294 stored in healthcare provider distributed database (blockchain) 190.

In various embodiments, the methods of the present disclosure may compare additional data stored in ingestible medical device 100 and external device 145, besides patient identifier(s) and active agent identifier(s), to determine whether to instruct the active agent delivery module 110 to release an active agent. By applying these criteria, the methods of the invention may avoid various errors that can arise in the dispensing and administration of oral medications, including ensuring that the right medication is administered to the right patient; avoiding errors in patient identification due to relocation of patients; avoiding over-dosing; and administering medications at the right time. For example, the comparison can include data on locations of ingestible medical device 100 and external device 145, and data concerning medication regimen, dosages, drug allergies, etc.

In certain embodiments, ingestible device identifiers 200 may be programmable following manufacture. In these embodiments, ingestible device identifiers 200 may be determined after the identifier is produced, wherein the identifier may be field programmable, mass programmable, fuse programmable, or reprogrammable. For example, the ingestible medical device 100 can be produced with one or more uncoded identifier, and this uncoded identifier can be subsequently coded with a personal identifier 210 for a given patient or subject 150. Any convenient programming technology may be employed. In certain embodiments, the programming technology is RFID technology.

In certain embodiments, ingestible device identifiers 200 of given ingestible medication devices 100 may be programmed following manufacture upon the occurrence of various healthcare management events. Examples include encoding ingestible medical devices with personal identifier 210 for a given patient 150 during or in connection with admission of the patient 150; encoding ingestible medical devices with an active agent identifier 220 for a given dosage formulation when filling a prescription for the dosage formulation; encoding ingestible medical devices with data concerning medication regimen, dosages, drug allergies, etc. for a given patient 150 when filling a prescription for that patient; encoding ingestible medication devices during transport from a pharmacy to a nurse station using a transport carrier with embedded RFID reader; and encoding one or more ingestible medication devices 100 using a hand-held device 174 after a caregiver 170 confirms the identity of the patient 150, e.g., by scanning a wristband label 160.

Similarly, external devices 145 may be encoded with external device identifiers 250 in the context of various healthcare management events. For example, a wristband label 160 may be encoded with a wristband personal identifier 262 when issuing the wristband label to a given patient 150 during admission of that patient, and an RFID-enabled transport carrier 174 may be encoded with mobile reader active agent identifiers 274 for a number of ingestible medication devices 100 during the transport of these ingestible medication devices from a pharmacy to a nurse station.

Biosensors and Personal Electrical Signals

In certain embodiments, cardiac sensors or other biosensors provide personal electrical signals that can be used in identifying an authorized patient and triggering release of the active agent in the ingestible medication device. The term personal electrical signal is used to indicate that a signal is intimately associated with the subject such that it can be used to confirm the identity of the subject for purposes of authentication. Personal electrical signals include, without limitation, physiological signals associated with the subject, transbody conductive signals generated by an ingestible marker device 100, transbody conductive signals generated by a body-associated device, e.g., an adhesive patient sensor patch 154 that is applied on the body of the subject 150, any object in physical contact with the subject for example watch, bracelet, necklace, ring, etc., and/or transbody conductive signals generated by an implanted body-associated device (not shown) that is located within the body of the subject 150. Physiological signals include, without limitation, skin impedance, electro cardiogram signals, conductively transmitted current signal, position of wearer, temperature, heart rate, perspiration rate, humidity, altitude/pressure, global positioning system (GPS), proximity, bacteria levels, glucose level, chemical markers, blood oxygen levels, among other physiological and physical parameters. Transbody conductive signals include, without limitation, electrical currents that are transmitted through the body of a subject, where the body acts as the conduction medium.

In certain embodiments, the system and method for ingestible drug delivery includes a cardiac monitoring element. The cardiac monitoring element can be an implanted cardiovascular device. The cardiac monitoring system can also be positioned as an external device. By example, this device could be positioned by a harness that is worn outside the body and has one or more electrodes that attach to the skin at different locations. Additionally, a cardiac monitoring device can be linked to a portable device, for example a watch that has one or two electrodes dispersed on the wrist.

In certain embodiments the systems include an external device that is distinct from the receiver (which may be implanted or topically applied in certain embodiments), where this external device provides a number of functionalities. For example, the device can read out information generated by ingestible medication devices and/or by psychological sensing devices, such as signals produced internally by a pacemaker device or a dedicated implant for detection of the pill. The purpose of the external apparatus is to transmit the data out of the patient and into an external electronic device, e.g., to a remote location such as a clinician.

In certain methods for tracking and administering ingestible medication devices, biosensors e.g., in patient sensor patch 154, can be used in monitoring a patient's physiological functions. Examples of monitoring a patient's physiological functions using biosensors include blood oxygen level (oximetry), blood glucose concentration (glucometer), blood pressure (e.g., measurement of arterial blood pressure), and electrical activity of the heart (electrocardiography), among others. In an embodiment, biosensor signals are communicated to one or more of ingestible medication device 100, caregiver mobile electronic device 174, and healthcare provider's server 185, and are processed to determine whether to modify a medication regimen based upon regimen criteria predetermined criteria by a physician at the time of prescribing the medication regimen. In various embodiments, physiological signals that are indicative of patient symptoms and/or medication side effects cause a predetermined adjustment to medication dosage or other aspects of a medication regimen, e.g., to provide symptom relief or to avoid adverse side effects. In an embodiment, biosensor signals sensed by sensors 116 of a previously ingested medication device 100 cause an adjustment of medication regimen stored in device 100. In an embodiment, an adjustment of medication regimen stored in ingestible medication device 100 triggers release of active agent 112.

Healthcare Provider Network and Blockchain

Turning again to FIG. 1, in the present systems and methods for tracking and administering ingestible medication devices, the ingestible medication device 100 can communicate with various electronic devices via a wireless network 140. The patient and healthcare provider professionals (e.g., physician, nurse, pharmacist) can use these devices to communicate with the ingestible drug delivery device 100. In various embodiments, the healthcare provider network 140 uses blockchain technology for generating and manipulating healthcare datasets in a distributed database 190. In various embodiments, the system may also be deployed on a closed system network or server, such as in a hospital, hospice, or resident care center.

By using blockchain technology in wireless network 140, distributed databases such as distributed ledgers ensure the integrity of data by generating a chain of data blocks linked together by cryptographic hashes of the data records in the data blocks. For example, a cryptographic hash of at least a portion of data records within a first block, and, in some cases, combined with a portion of data records in previous blocks, is used to generate the block address for a new digital identity block succeeding the first block. As an update to the data records stored in the one or more data blocks, a new data block is generated containing respective updated data records and linked to a preceding block with an address based upon a cryptographic hash of at least a portion of the data records in the preceding block. In other words, the linked blocks form a blockchain that inherently includes a traceable sequence of addresses that can be used to track the updates to the data records contained therein.

The linked blocks, or blockchain, may be distributed among multiple network nodes within a computer network such that each node may maintain a copy of the blockchain. Data integrity is guaranteed by the virtue of multiple network nodes in a network having a copy of the same blockchain. A central trust authority is therefore not required to vouch for the integrity of the distributed database hosted by multiple nodes in the network.

Figure 4:
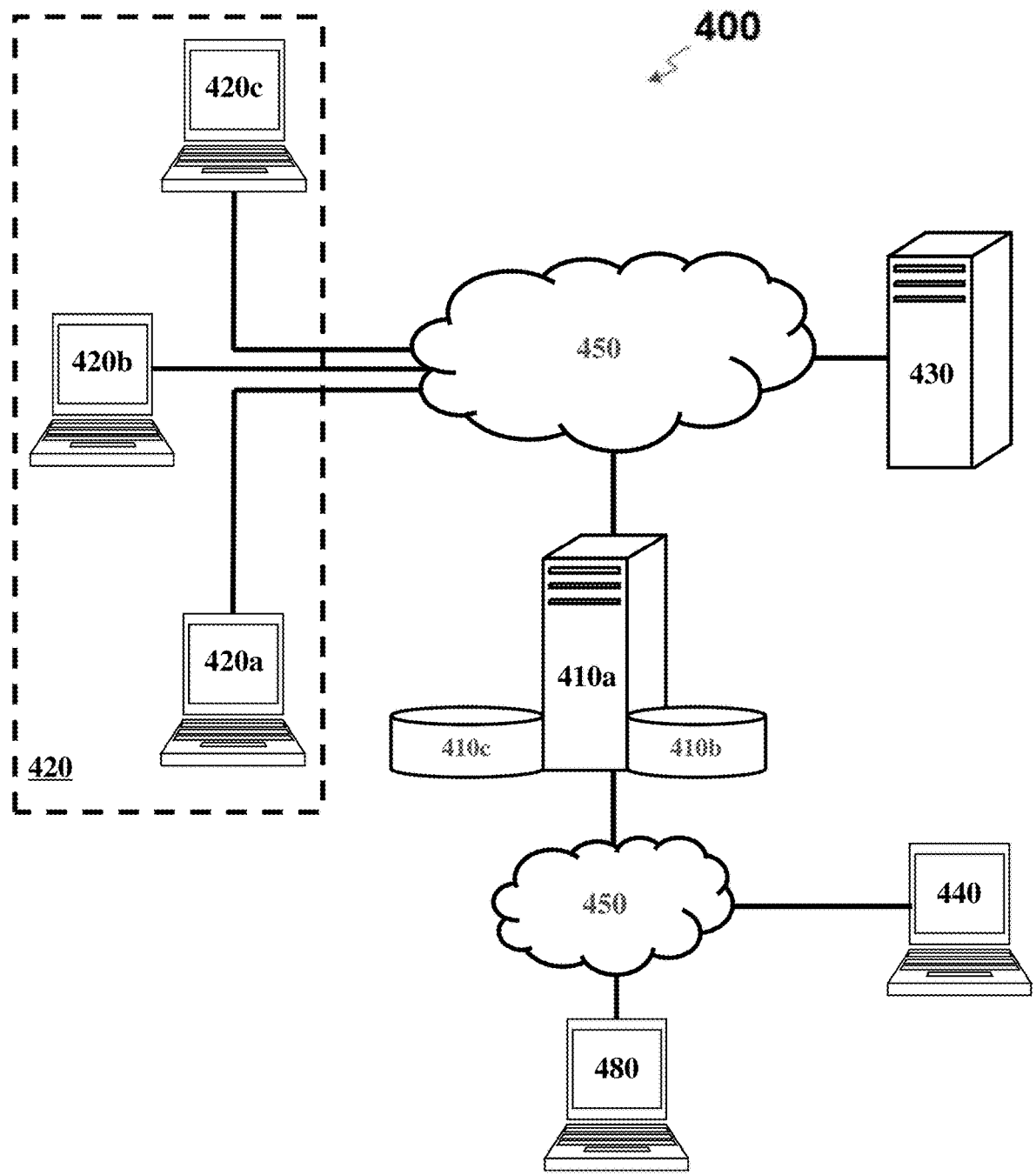
FIG. 4 illustrates an example of a computer system for generating an intelligent healthcare-based blockchain, according to an embodiment.

FIG. 4 illustrates components of a system 400 for generating an intelligent healthcare-related blockchain, according to an exemplary embodiment. The exemplary system 400 may comprise an analytics server 410a, system database 410b, a key storage database 410c, client devices 440, manager's device 480, third party database 430, and distributed network nodes 420a-c. Aspects of the system 400 may be configured to employ and manage a system blockchain, sometimes referred to in the art as a "distributed ledger," and may include blockchain-based distributed ledger software (e.g., Hyperledger, Ethereum, Openchain, and TerraLedger). The system blockchain may operate as a distributed database that stores data records associated with users and transaction documents, where the data records stored on the system blockchain may be blocks of data (e.g., block instances or blocks) that are hosted (e.g., locally stored or otherwise in possession of each distributed, such as being remotely hosted or hosted in a cloud) on distributed network nodes 420a-c.

The data stored in records within system database 410b may vary from the data stored in blocks of the system blockchain hosted on network nodes 420a-c. Furthermore, each block may not be accessible to other network nodes, however, all block instances may be accessed by the analytics server 410a and/or may be stored in the system database 410b. In some embodiments, the analytics server 410a may generate a duplicate of one or more block instances within a system blockchain and store said block instances in the system database 410b.

While the analytics server 410a may dictate accessibility and transmit instructions to other parties within system 400, each network node within the distributed network nodes 420a-c (e.g., creator of the block instance) or a client device 440 may prevent others within system 400 from accessing at least portions of the data within one or more block instances. In various embodiments, while generating a block instance, a portion of the data within the block instance may be designated as private. For example, a portion of the blockchain may be encrypted so one or more network nodes are unable to access the encrypted portion.

The analytics server 410a may also generate, access, and update blockchain instances hosted on network nodes 420a-c, according to instructions received from a client devices 440, manager's device 480, and/or any of the nodes within the network nodes 420a-c. Software executed by the analytics server 410a may provide blockchain services to users interacting with the analytics server 410a.

Analytics server 410a may generate and display a user interface on client devices 440, each node within the distributed network nodes 420a-c, and healthcare manager's device 480. An example of the user interface generated and hosted by the analytics server 410a may be a website. The website may be used to generate and access data stored on a system database 410b or a blockchain hosted by nodes 420a-c and managed by the analytics server 410a. A graphical user interface may act as an intermediary between different parties involved with a participant's medical care and may be a central and "one stop" place for adding, updating, and/or retrieving healthcare data. While the graphical user interface is described herein as a central management tool, neither the analytics server 410a nor the graphical user interface deviates from the spirit of the distributed nature of the blockchain technology.

The analytics server 410a may also generate each new block instance with a timestamp or other data that links the new block instance with existing block instances on the blockchain. As an example, when the analytics server 410a generates a new user record in the system database 410b, the analytics server 410a then generates a hash value for the user based upon one or more data fields of the user record. The analytics server 410a may then generate a new block instance for the system blockchain within the local instance of the blockchain stored in the analytics server 410a (or a database associated with the analytics server 410a. The analytics server 410a then transmits the updated block instance to each respective network node 420a-c.

A network node may generate new blocks on a locally stored instance of the system blockchain according to data received from an analytics server 410a or other network nodes 420a-c. The network nodes 420a-c may update the local instances of the blockchain stored on each of the network nodes 420a-c by appending a block instance newly generated by the analytics server 410a to the existing blockchain. In some instances, the analytics server 410a may update a local block instance stored on the analytics server 410a (e.g., within the system database 410b), and then instructs one or more of the network nodes 420a-c to update the blockchain stored in their local storage (e.g., local database).

Even though all network nodes may possess the blockchain, not all network nodes may access the data within the blockchain. The analytics server may generate a customized encryption based on a network node's selection of data. For some healthcare information, the analytics server may transmit the data to the all the other network nodes associated with the blockchain. All network nodes may freely share the public information. On the other hand, a network node may designate a portion of the data in a block instance as private.

In those embodiments, the analytics server may encrypt the data, e.g., using a network node's public key. This encryption allows the data to be transmitted and stored onto all the network nodes within the blockchain. However, only the network nodes having proper authorization to decrypt the data may view and access the encrypted data. In this way, sensitive patient data (e.g., social security numbers, medical histories, and the like) may be included within the blockchain without compromising the participant's privacy.

A key storage database 410c, sometimes referred in the art as a high security module, key appliance, certificate authority, or the like, may be a computing device configured to manage and distribute encryption keys and cryptographic certificates to various computing devices in the system 400 according to predetermined user roles and existing rules. In some implementations, encryption keys may be used for authentication of users when users log into a website (or any other user interface provided to the users) hosted on the analytics server 110a. In some implementations, encryption keys may be used to encrypt the data within the block instance of the system blockchain and to prevent unauthorized access. Additionally or alternatively, encryption keys may be used to confirm or "sign" data transfers or to confirm that the data originated from a known party. Encryption keys may be also used by users at an application level to apply a digital signature to a document or contract, which, in some cases, may trigger instructions from script code of a smart contract stored on the system blockchain.

TABLE 1

Healthcare Management Events -
Network Nodes, Devices Accessing Blockchain

| NODE, DEVICE | HEALTHCARE MANAGEMENT EVENT |
|---|---|
| Administration | Updating patient medical history with patient data collected during patient admission |
| Administration | Issuing a patient wristband including personal identifiers, patient medical history, assigned room, etc. |
| Administration | Issuing updated patient wristband upon moving the patient to a new room |
| Physician Order Entry ("CPOE") system | Creating an electronic prescription via CPOE system |
| Physician Order Entry ("CPOE") system | Changing medication regimen via CPOE system based upon patient symptoms or responses to caregiver symptom queries |
| ePrescribing System | Filling a prescription based on CPOE data and patient medical data (medication allergies, etc.) |
| Nursing Station | Delivering prescribed ingestible medication devices to a nursing station or other caregiver site |
| Handheld Caregiver Device | Downloading medication regimen data for an identified patient to a handheld caregiver device |
| Handheld Caregiver Device | Sensing an ingestible device identifier or wristband identifier via a handheld caregiver device |
| Handheld Caregiver Device | Recording patient responses to symptoms and functions queries via a handheld caregiver device |
| Fixed RFID Reader | Authenticating a patient for release of an active agent based upon patient location data |
| Fixed RFID Reader | Sensing one or more ingestible device identifier(s) following administration via a fixed RFID reader |
| Patient Wristband | Writing ingestible device identifier(s) to a patient wristband |
| Patient Wristband | Authenticating a patient for release of an active agent based upon patient wristband data |
| Ingestible | Programming an ingestible device identifier to an |

TABLE 1-continued

Healthcare Management Events -
Network Nodes, Devices Accessing Blockchain

| NODE, DEVICE | HEALTHCARE MANAGEMENT EVENT |
|---|---|
| Device Manufacturer | ingestible medication device during manufacture |
| Ingestible Device | Reprogramming an ingestible device identifier to an ingestible medication device following manufacture |
| Ingestible Device | Actuating release of an active agent from an administered ingestible medication device |

As shown in Table 1, the exemplary system 400 may generate and manipulate datasets stored in blockchains in connection with various healthcare management events. In various embodiments, healthcare system 400 tracks real-time events relating to ordering, dispensing, and administration of medications, and continuously tracks the context of patients as it relates to their healthcare management. Each healthcare management event is stored on the blockchain to ensure ownership of the data. Various devices of healthcare network 400 may serve as network nodes 420, client devices 440, or other devices that access blockchains. In exemplary embodiments, network nodes 420 can include healthcare administration database 420a, ePrescribing system with computerized physician order entry (CPOE) system 420b (e.g., hospital pharmacy), and caregiver (nursing) stations 420c. In exemplary embodiments, client devices 440 include handheld caregiver devices 174, fixed RFID readers 178, patient wristbands 160, and ingestible medication devices 100. In exemplary embodiments, third party database 130 includes an ingestible device manufacturer database. Various embodiments employ digital marking of ingestible medication devices 100 with the secure distributed ledger technology of blockchain to reduce fraud and manage quality in manufacturing and distribution of the ingestible medication devices.

Blockchain-based healthcare management system 400 is resilient, ensuring continuing reliable operation when an equipment failure, power outage or other disruption causes failure of one or more nodes. In an exemplary application, using mobile electronic devices 174 and healthcare provider terminals 180, physicians, caregivers and other healthcare professionals may access data from the database/blockchain to manage ordering, dispensing, and oral administration of ingestible medications. In various embodiments, blockchain implements coding of electronic prescriptions, medication regimens, medication allergies, etc. as specific conditions for administration of ingestible medication devices 100 to patients 150.

Tracking and Administering Using Ingestible Medication Devices

In various embodiments, one or more ingestible medication devices 100 and one or more external devices 145 perform a plurality of processes for tracking and administering patient access to orally administered medications. While the blocks in the disclosed processes are shown in a particular order, the actual order may differ. In some embodiments, some steps may be performed in parallel.

Limited Range RFID Patient Wristbands

In some embodiments, one or more ingestible medication devices 100 communicate with external devices 145, such as RFID-enabled patient wristbands 160, to track ingestible medication devices 100 and to administer patient access to orally administered medications.

These methods rely on proximity of an RFID-enabled wristband, or other external device, to associate the device with a patient that has been administered ingestible medication device 100. In an embodiment, if an ingestible medication device 100 detects an RFID-enabled wristband 160 within a limited read range, that detection may strongly indicate that the wristband 160 is worn by a patient 150 that has ingested the ingestible medication device 100. In another embodiment, if ingestible medication device 100 detects a fixed RFID reader 178 within its read range, that may indicate that the fixed RFID reader 178 is located in the room and/or near the bed of patient 150. These inferences can be applied to various location-based processes for tracking and administering ingestible medication devices 100. For external devices 145 within the read range of ingestible medication device 100, these methods can compare various ingestible device identifiers with external device identifiers to determine whether or not to release an active agent of the ingestible medication device 100 to a human subject that has ingested the device 100.

Figure 5:
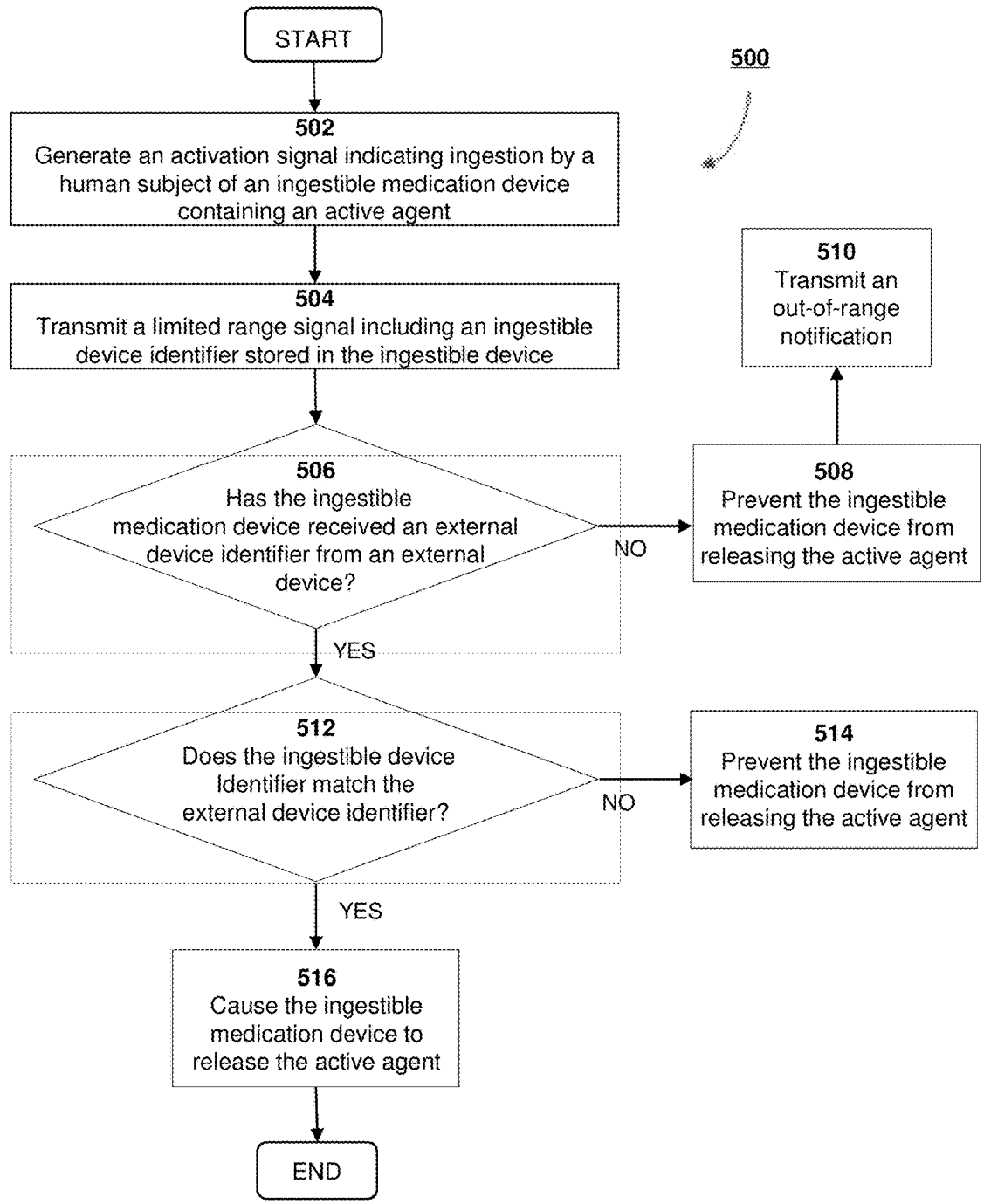
FIG. 5 is a flow chart schematic diagram of a method for tracking and managing administration of an ingestible drug delivery device using limited-range wireless communications, according to an embodiment.

In the method 500 of FIG. 5, at 502 a processor of the ingestible medication device generates an activation signal. The activation signal indicates ingestion of the ingestible medication device by a human subject, wherein the ingestible medication device contains an activation agent designed to product a physiological result in human beings. In some embodiments, the activation signal is emitted by an activation component of a power source, which is activated following ingestion of the ingestible medication device. For example, the activation component can activate the power source upon experience of a stimulus, e.g., contact of the composition with a target physiological site of interest, such as the stomach. In an embodiment, the activation signal can be sensed by external devices, or external devices within a limited range, signaling that that the ingestible medication device 100 has been ingested and that electronic components of the ingestible medication device 100 have been activated.

At 504, the processor of the ingestible medication device transmits a limited range signal that includes an ingestible device identifier stored in the ingestible medication device. In certain embodiments, an ingestible device identifier is a component that emits a signal upon activation by a stimulus, e.g., by interrogation, upon contact with a target physiological location, etc. In an embodiment, the ingestible device identifiers include a personal identifier associating a given ingestible medication device with a given patient 150 or other subject. In certain embodiments, ingestible device identifiers includes an active agent identifier(s), i.e., data identifying an active agent, stored in active agent delivery module or otherwise contained in the ingestible medical device.

In one embodiment, the limited-range signal transmitted by the ingestible medication device is an RFID signal in the UHF frequency band. For example, a patient wristband 160 worn by patient 150 may receive a limited-range signal from an ingestible medication device that has been ingested by the patient, whereas a patient wristband in a different room of the healthcare institution would not receive the limited range signal. In one embodiment, the limited range signal has a range no greater than 3 m. In another embodiment, the limited range signal has a range no greater than 2 m. In a further embodiment, the limited range signal has a range no greater than 1 m. In various embodiments, successful transmission or receipt of the limited range signal indicates proximity of the patient 150 (and any ingestible medication device 100 ingested by the patient) to the external device 145, and may be used in various methods for management of ingestible medication devices 100 based upon localization of patients 150 and/or external devices 145.

At 506, the processor of the ingestible medication device determines whether the device has received an external device identifier from one or more external device, in response to the transmission of the limited range signal. If the processor fails to detect an external device identifier, the processor prevents 508 the ingestible medication device from releasing the active agent, and transmits an out-of-range notification 510. For example, the out-of-range notification can be transmitted to healthcare provider server 185 to update health provider blockchain 190.

In the event the ingestible medication device processor detects an external device identifier at 506, at 512 the processor determines whether the ingestible device identifier matches an external device identifier received from an external device. If the ingestible device identifier and the external device identifier do not match at 512, the processor prevents 514 the ingestible medication device from releasing the active agent. If the ingestible device identifier successfully matches an external device identifier at 512, the processor causes 516 the ingestible medication device to release the active agent. The method 500 then ends.

Figure 6:
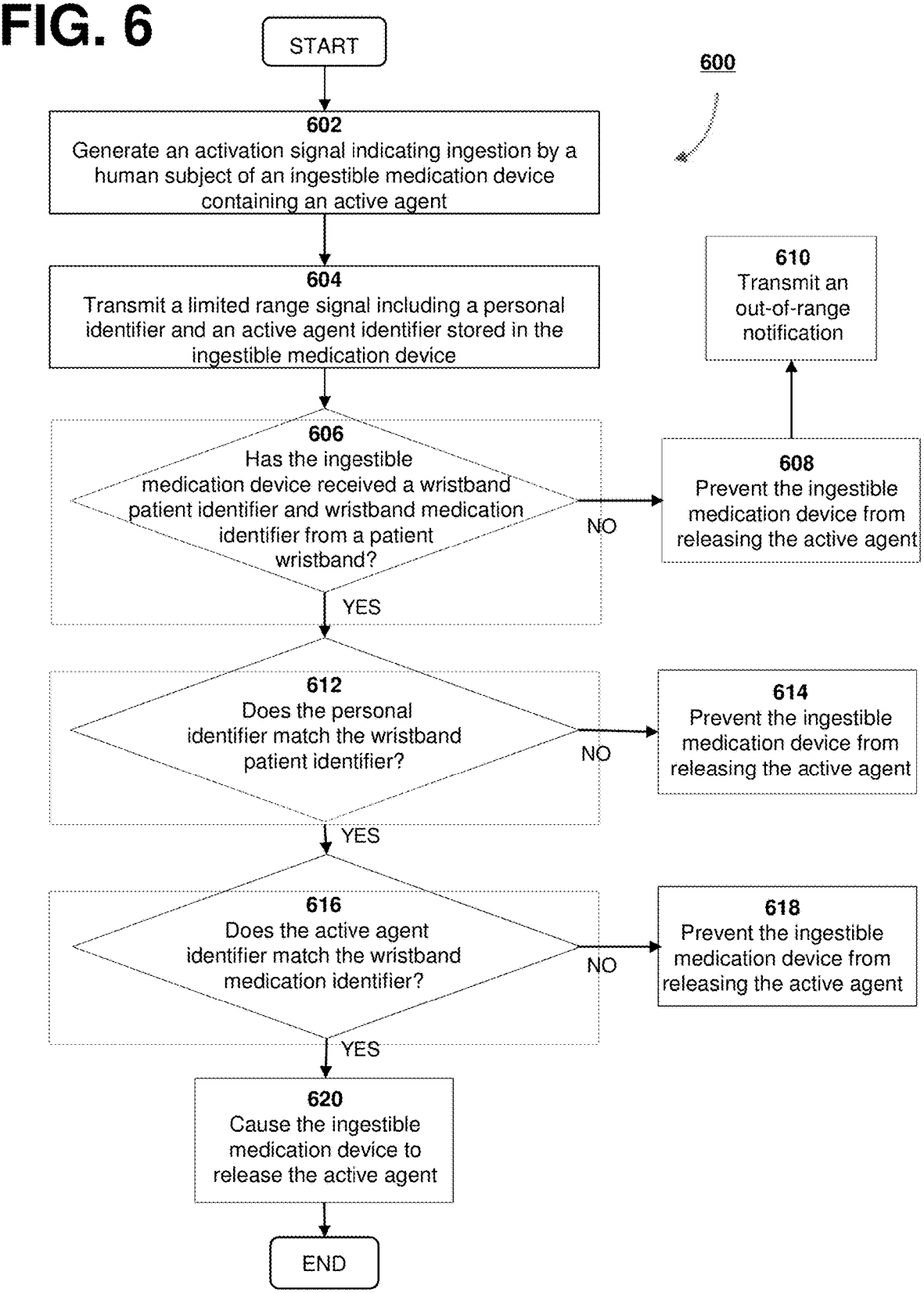
FIG. 6 is a flow chart schematic diagram of a method for tracking and managing administration of an ingestible drug delivery device using limited-range radio frequency identification communications, according to an embodiment.

The method 600 of FIG. 6, similar to the method 500, uses limited range communications of ingestible medication device 100 to detect a patient wristband 160 in proximity to ingestible medication device 100. Upon sensing such device, the method compares one or more ingestible device identifier(s) with external device identifiers of the patient wristband to determine whether or not to release an active agent of the ingestible medication device 100 to a human subject. At 602 a processor of the ingestible medication device generates an activation signal, using processes similar to those discussed for step 502.

At 604, the processor of the ingestible medication device transmits a limited range signal that includes both a personal identifier, and an active agent identifier, stored in the ingestible medication device. In certain embodiments, the ingestible device identifier is a component that emits a signal upon activation by a stimulus, e.g., by interrogation, upon contact with a target physiological location, etc. In an embodiment, personal identifier associates the ingestible medication device 100 with a given patient 150 or other subject. In an embodiment, the active agent identifier identifies an active agent, stored in active agent delivery module or otherwise contained in the ingestible medical device 100. Various personal identifiers and active agent identifiers are discussed above with reference to the embodiments of FIGS. 1-3.

At 606, the processor of the ingestible medication device determines whether the device has received an wristband identifier 260 from a patient wristband 160, in response to the transmission of the limited range signal. If the processor fails to detect a wristband identifier, the processor prevents 608 the ingestible medication device from releasing the active agent, and transmits an out-of-range notification 610. For example, the out-of-range notification can be transmitted to healthcare provider server 185 to update health provider blockchain 190.

In the event the ingestible medication device processor detects a wristband identifier at 606, at 612 and 616 the processor carries out two comparisons of ingestible device identifiers with wristband identifiers. In the first comparison, if the personal identifier 210 and the wristband patient identifier 262 do not match at 612, the processor prevents 618 the ingestible medication device from releasing the active agent.

If the personal identifier 210 successfully matches an wristband patient identifier 262 at 612, the method proceeds to the second comparison at 616. If the active agent identifier 220 and the wristband medication identifier 264 do not match at 616, the processor prevents 618 the ingestible medication device from releasing the active agent. If the active agent identifier 220 successfully matches the wristband medication identifier 264 at 616, processor causes 620 the ingestible medication device to release the active agent. The method 600 then ends.

Hand Held Caregiver Devices

In some embodiments, a nurse or other caregiver 170 administers one or more ingestible medication devices 100 to a human subject, and tracks ingested medication devices 100 using a hand held caregiver device 174 and/or RFID-enabled patient wristband 160. These methods enable a nurse or other caregiver to track medication information and communicate active agent identifiers or other medication data stored in the administered ingestible medication devices 100, and to control the administration of ingested medication device 100 by confirming that the stored medication information complies with medication regimen and dosage agent stored for the human subject in external devices (e.g., blockchain database 190) of the healthcare provider institution.

Figure 7:
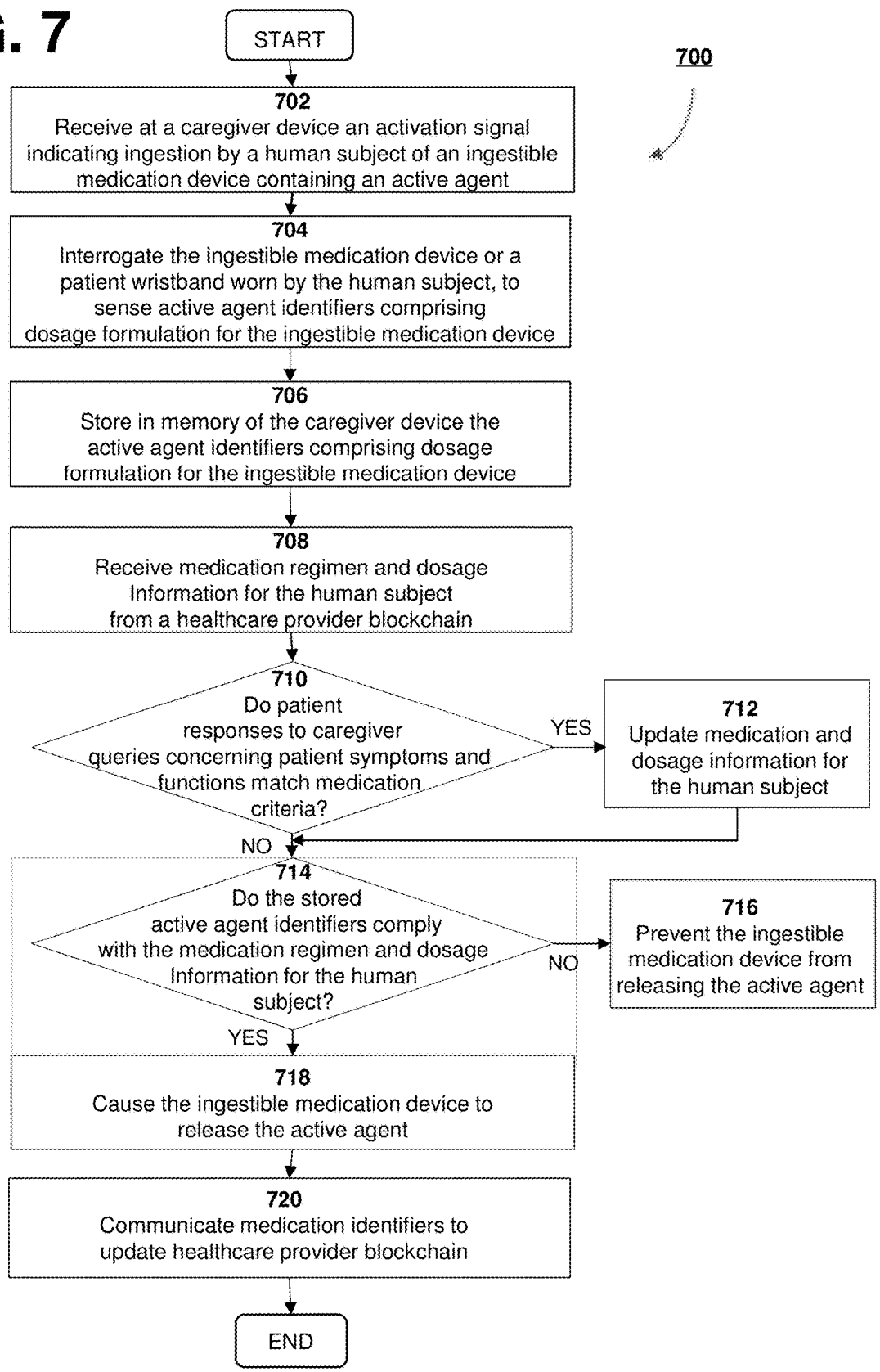
FIG. 7 is a flow chart schematic diagram of a method for managing administration of an ingestible drug delivery device by monitoring compliance with medication regimen and dosage information, according to an embodiment.

In the method 700 shown in FIG. 7, a processor of a caregiver device 174 tracks active agent identifiers of an ingestible medication device 100 administered to a human subject. The processor compares this data with medication regimen and dosage information for the human subject downloaded from the healthcare provider system (blockchain database 190). This comparison determines whether or not the administered medication complies with the regimen and dosage information. In the event of a positive comparison, the caregiver device sends a signal to ingestible medication device 100 authorizing the ingestible medication device to release the active agent.

At 702 a processor of the caregiver hand held device receives an activation signal, using processes similar to those discussed for step 502. The activation signal indicates ingestion of the ingestible medication device by a human subject, wherein the ingestible medication device contains an activation agent designed to product a physiological result in human beings, and may be similar to the activation signal discussed for step 502 of the method of FIG. 5.

At 704, a wireless communication module of the caregiver device interrogates the processor of the ingestible medication device, or alternatively interrogates a patient wristband of the human subject. This interrogation senses active agent identifiers of the ingestible medication device, comprising dosage formulation data. In one embodiment of step 704, an RFID reader of the caregiver device interrogates an RFID marker contained in the ingestible medication device to sense the active agent identifiers. In another embodiment of step 704, an RFID reader of the caregiver device interrogates a wristband device contained in the patient wristband worn by the human subject. The wristband device includes an RFID label that stores the active agent identifiers, and the RFID reader interrogates the active agent identifiers stored in the RFID label. At step 706, the caregiver device stores the active agent identifiers in memory.

At step 708, the caregiver device receives medication regimen and dosage information for the human subject from the healthcare provider's computer system 185. In an embodiment, the medication regimen and dosage information is downloaded from blockchain database 190 of the healthcare provider.

Optional steps 710, 712 are included in method 700 if a prescribing physician has defined a medication procedure. As used in the present disclosure, a medication procedure includes predetermined criteria under which a medication regimen and/or dosage may be modified or updated, and defined modifications or updates of the medication regimen and/or dosage upon occurrence of the predetermined criteria. Typically, the predetermined criteria under which a medication regimen and/or dosage may be modified are based upon patient symptoms and/or side effects of medication. The medication procedure comprises a set of rules suitable for execution by a computer.

In an embodiment, patient responses to caregiver queries based upon the medication procedure may cause the system to update medication regimen information for the patient. Typical medication procedures may dictate modifying a medication regimen, such as to increase individual dosages of ingestible medication devices 100 or increase the frequency of administration of ingestible medication devices 100, in order to relieve patient symptoms such as pain. Additionally, medication procedures may dictate modifying a medication regimen in the event of adverse side effects or impaired patient functionality due to medication, such as to decrease individual dosage amounts in this circumstance.

In various embodiments, a blockchain correlation engine of the healthcare management system 140 generates standardized queries for display by a user interface of caregiver handheld device 174 in accordance with a medication procedure stored in the computerized physician order entry system. The blockchain correlation engine also may act upon data from other modules, such as patient data and medication data, in generating caregiver queries. The user interface of caregiver handheld device 174 may include a form for entering patient query responses, such as patient estimates of symptom severity. In the event 712 that patient query responses match criteria in a medication procedure for modifying the medication regimen as predetermined by the physician, the system updates the medication regimen in accordance with the medication procedure. Step 712 may include updating the medication regimen stored by the caregiver handheld device 174, as well as uploading the updated medication regimen for appending to the healthcare provider blockchain.

In other embodiments, a medication procedure stored in the computerized physician order entry module includes criteria for updating a medication regimen based upon medication requests received from patients. Typically such criteria involve a pattern of patient requests for medication that indicates a patient need for symptom relief, such as relief from pain. For example, a patient 150 may request administration of an ingestible medication device 100 by communicating this request to a nurse or other caregiver 170 using a nurse call device 152. In an embodiment, one or more patient medication request matches criteria in a medication procedure for modifying the medication regimen as predetermined by the physician. In this event, system updates the medication regimen 712 in accordance with the medication procedure. In another embodiment, a patient medication request communicated to a caregiver 170, together with an evaluation of the medication request centered by the caregiver into handheld device 174, match criteria in a medication procedure for modifying the medication regimen. In this event, the system updates the medication regimen 712 in accordance with the medication procedure.

In further embodiments, the system updates medication regimen information for the patient based upon physiological signals received by caregiver handheld device 174 from biosensors monitoring the patient. For example, caregiver device 174 may receive physiological signals from biosensors of sensor patch 154 worn by the patient. Caregiver device 174 may compare these signals with criteria in a medication procedure, e.g., based upon physiological signals indicative of patient symptoms. At step 712, the system may modify the patient's medication regimen based upon automated processing of patient physiological data, or may modify the patient's medication regimen following caregiver review of the patient physiological data.

At step 714, the processor of caregiver handheld device 174 determines whether the active agent identifiers stored at step 706 comply with the medication regimen and dosage information received at step 708, or if applicable with updated medication regimen and dosage information generated at step 712. If these data do not match, the care provider processor transmits a signal to the ingestible medication device preventing 716 the device from releasing the active agent. If these data match successfully, the caregiver processor transmits an authorization signal to ingestible medication device causing 718 the ingestible medication device to release the active agent.

At 720, the caregiver device communicates 720 the medication identifiers to the healthcare provider's system 185 to update the healthcare provider blockchain 190. In various embodiments, the caregiver device communicates to the healthcare provider system a request to update a patient record corresponding to the human subject, the patient record corresponding to a first blockchain stored on a plurality of network nodes of the healthcare provider system. The request instructs the healthcare provider system to append to the first blockchain a second blockchain including the active agent identifiers comprising the dosage formulation information for the ingestible medication device. Method 700 then ends.

Figure 8:
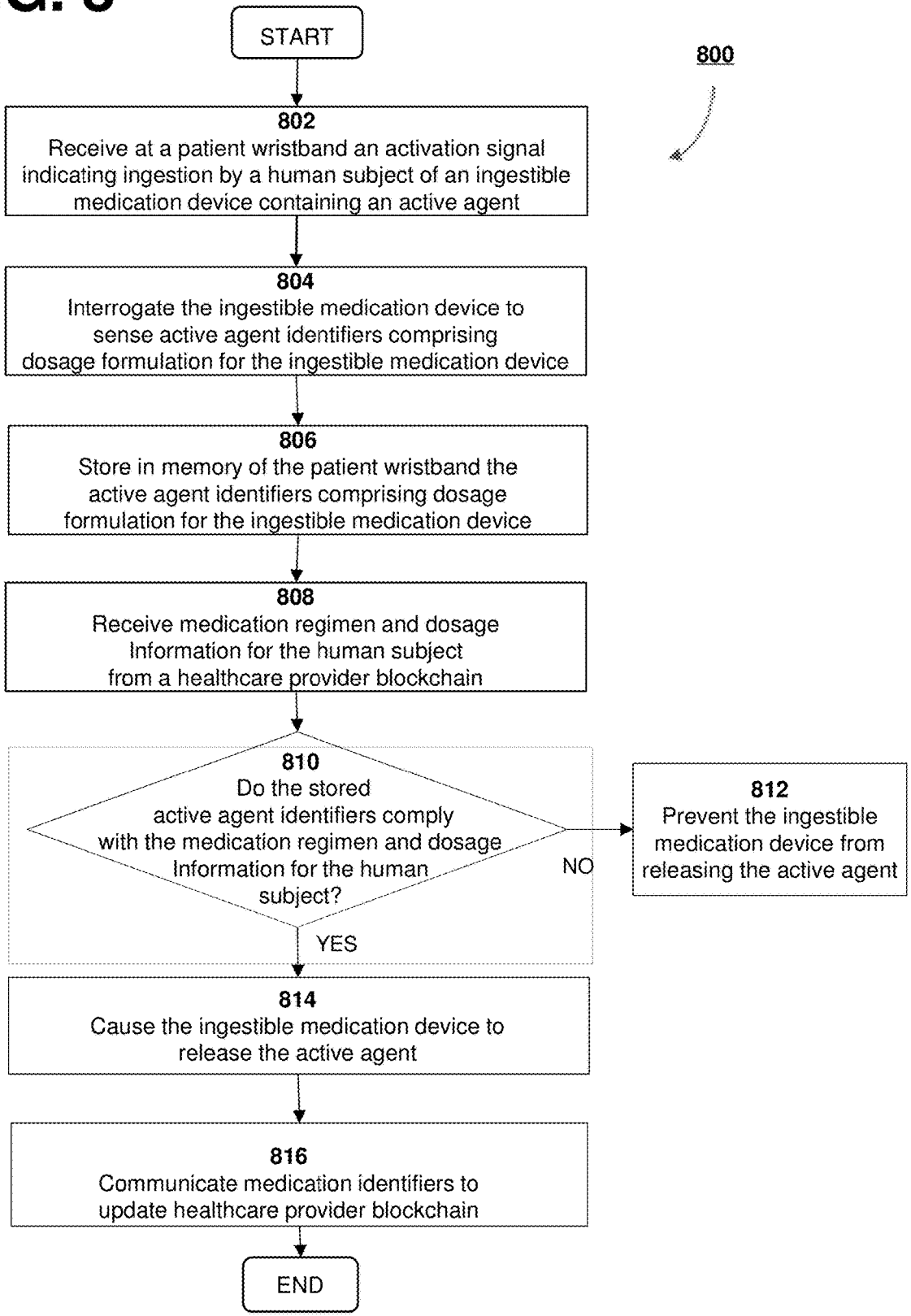
FIG. 8 is a flow chart schematic diagram of a method for managing administration of an ingestible drug delivery device by monitoring compliance with medication regimen and dosage information, according to an embodiment.

In the method 800 shown in FIG. 8, a processor of a patient wristband 160 worn by the human subject 150 tracks active agent identifiers of an ingestible medication device 100 administered to that human subject. The processor compares this data with medication regimen and dosage information for the human subject received from the caregiver device 174, or alternative from the healthcare provider system. This comparison determines whether or not the administered medication complies with the regimen and dosage information. In the event of a positive comparison, the processor of patient wristband sends a signal to ingestible medication device 100 authorizing the ingestible medication device to release the active agent.

At 802 a processor of the patient wristband receives an activation signal, using processes similar to those discussed for step 502. The activation signal indicates ingestion of the ingestible medication device by a human subject, wherein the ingestible medication device contains an activation agent designed to product a physiological result in human beings, and may be similar to the activation signal discussed for step 502 of the method of FIG. 5.

At 804, a wireless communication module of the caregiver device interrogates the processor of the ingestible medication device to sense active agent identifiers of the ingestible medication device, comprising dosage formulation data. In one embodiment, the wristband device includes an RFID label that stores the active agent identifiers, and the RFID reader interrogates the active agent identifiers stored in the RFID label. At step 806, the patient wristband stores the active agent identifiers in memory.

At step 808, the patient wristband receives medication regimen and dosage information for the human subject from the healthcare provider's computer system 185. In an embodiment, the patient wristband receives the medication regimen and dosage information from the caregiver device 174. In another embodiment, the medication regimen and dosage information is downloaded from blockchain database 190 of the healthcare provider.

At step 810, the processor of patient wristband 160 determines whether the active agent identifiers stored at step 806 comply with the medication regimen and dosage information received at step 808. If these data do not match, the caregiver processor transmits a signal to the ingestible medication device preventing 812 the device from releasing the active agent. If these data match successfully, the caregiver processor transmits an authorization signal to ingestible medication device causing 814 the ingestible medication device to release the active agent.

At 816, the caregiver device communicates the medication identifiers to the healthcare provider's system 185 to update the healthcare provider blockchain 190. Method 800 then ends.

Computerized Physician Order Entry and Prescription Fill Process

In some embodiments, a doctor, nurse or other healthcare professional uses computerized physician order entry (CPOE) and prescription fill processes to track prescribed medications including ingestible medication devices 100. In one embodiment, computerized prescription fill processes include cart-fill methods that rely upon RFID-enabled transport carriers or carts for transporting ingestible medication devices to a nurse station or other caregiver station of a healthcare care facility.

In an embodiment, healthcare provider system 140 includes a CPOE module to capture physician orders for ingestible medication to be administered to a given patient, and physician instructions for this administration, such as medication regimens. Prescribed medication regimens include, for example, individual dosage amounts, frequency of administration, and minimum dosing intervals. In an embodiment, healthcare provider system 140 also includes ePrescribing functions. For example, ePrescribing data may alert physicians and clinicians to a particular patient's drug allergies and current medications. As "ePrescribing system" is used in the present disclosure, the system may incorporate CPOE functions, allowing treating physicians to enter patient data electronically when entering medication orders.

Figure 9:
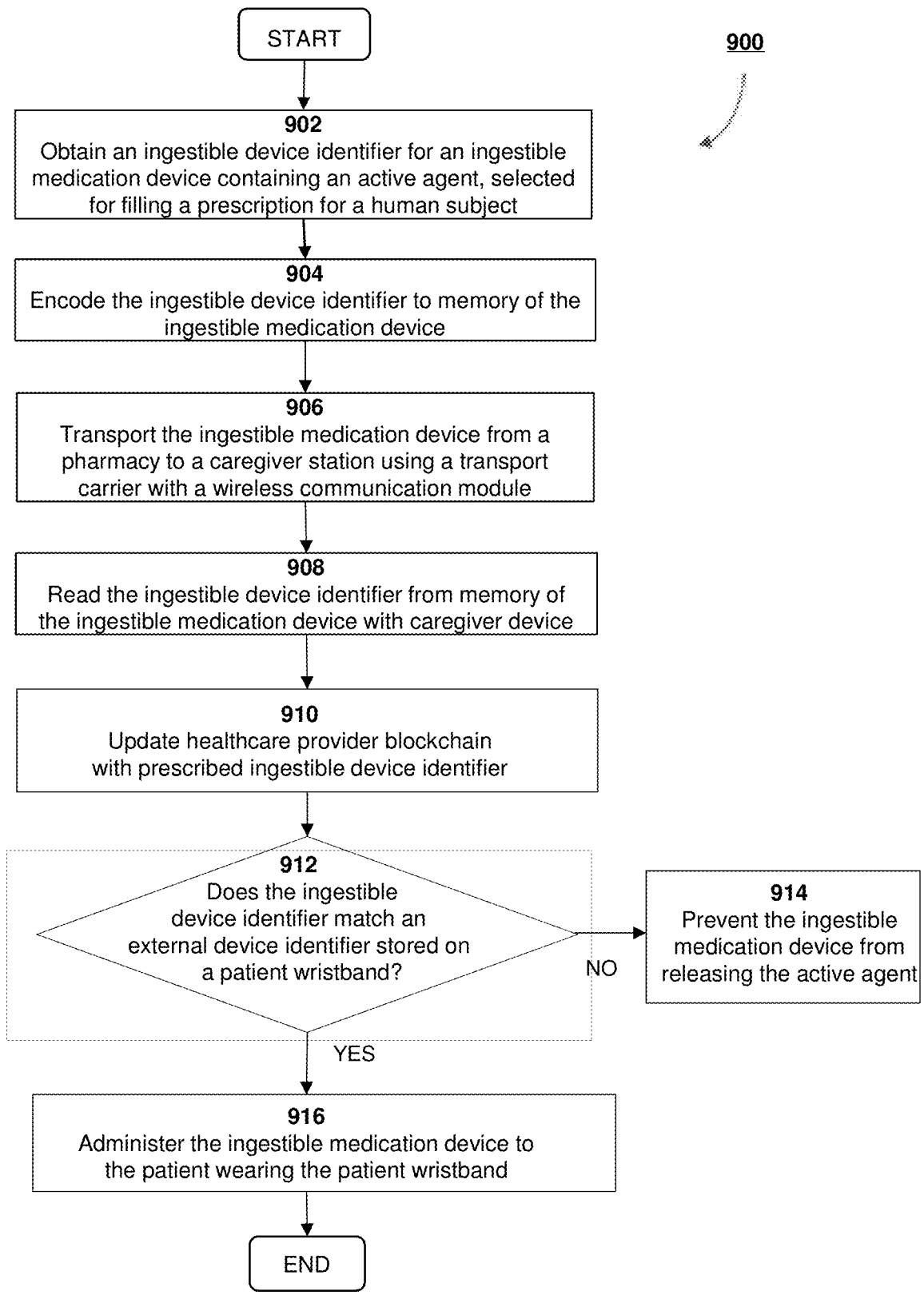
FIG. 9 is a flow chart schematic diagram of a method for tracking and administering an ingestible drug delivery device selected in filling a prescription, according to an embodiment.

In the method 900 of FIG. 9, at 902 a processor of the healthcare provider obtains an ingestible device identifier for an ingestible medication device selected for filling a prescription of a human subject. In an embodiment, the processor of the healthcare provider is a computer system of a healthcare provider pharmacy. In an embodiment, the processor obtains the ingestible device identifier from an ePrescribing system of the healthcare provider. In various embodiments, the ingestible device identifier includes one or more of a personal identifier and an active agent identifier, among other possibilities.

In various embodiments of step 902, the processor of the healthcare provider may obtain additional data from the ePrescribing system to be stored in ingestible medical device 100, besides patient identifier(s) and active agent identifier(s), based upon instructions from the prescribing physician and/or patient medical history. In some embodiments, the ingestible device identifier may include medication regimen information, which may be included in the active agent identifier, or separate therefrom. In some embodiments, the ingestible device identifier also includes a medication procedure.

At 904 the healthcare provider encodes a memory in communication with a processor of the ingestible medication device with the ingestible device identifier. In one embodiment, the healthcare provider encodes the ingestible medication device while filling the prescription at the pharmacy. In another device, the healthcare provider encodes the ingestible medication device using a transport carrier that transports the ingestible medication device and other medications from the pharmacy to a caregiver station, wherein the transport carrier includes a wireless communication module. In one embodiment, the transport carrier includes an RFID reader that can read RFID markers of ingestible medication devices housed in the carrier.

In embodiments of step 902 in which the processor of the healthcare provider obtains additional data from the ePrescribing system to be stored in ingestible medical device 100 besides patient identifier(s) and active agent identifier(s), at step 904 the healthcare provider encodes a memory in communication with a processor of the ingestible medication device with this additional data.

At 906 the transport carrier transports the ingestible medication device from the pharmacy to a caregiver station. At 908, a caregiver device reads the ingestible device identifier from memory of the ingestible medication device, or from the transport carrier.

At 910, the healthcare provider blockchain 190 is updated to include a transaction for the prescribed ingestible medication device and the ingestible device identifier. In various embodiments, the caregiver device generate s a request to update a patient record corresponding to the human subject, the patient record corresponding to a first blockchain stored on a plurality of network nodes of a system of the healthcare institution. The request instructs the provider system to append to the first blockchain a second blockchain including a transaction of encoding the ingestible device identifier to the memory of the ingestible medication device.

At 912, the caregiver device compares the ingestible device identifier with an external device identifier stored on a patient wristband label worn by a patient, to confirm whether or not to administer the ingestible medication device to the patient. If these data do not match, at 914 the caregiver device issues a signal to the ingestible medication device preventing release of the active agent. If the ingestible device identifier successfully matches the external device identifier of the RFID wristband at 916, the caregiver administers the ingestible medication device to the patient wearing the patient wristband. The method then ends.

In embodiments of step 902 in which the processor of the healthcare provider obtains additional data obtained from the ePrescribing system to be stored in ingestible medical device 100, besides patient identifier(s) and active agent identifier(s), step 912 is adapted accordingly. In these embodiments, at 912 when the caregiver device compares the ingestible device identifier with an external device identifier stored on a patient wristband label worn by a patient, the comparison also includes the additional data from the ePrescribing system, such as medication regimen information. In these embodiments, the patient wristband label also stores the additional data from the ePrescribing system, such as medication regimen information for the patient wearing the patient wristband label.

In the method 1000 of FIG. 10, at 1002 a processor of the healthcare provider obtains an personal identifier and an active agent identifier for an ingestible medication device selected for filling a prescription of a human subject. In an embodiment, the processor of the healthcare provider is a computer system of a healthcare provider pharmacy. In an embodiment, the processor obtains the personal identifier and the active agent identifier from an ePrescribing system of the healthcare provider.

In various embodiments of step 1002, the processor of the healthcare provider may obtain additional data from the ePrescribing system to be stored in ingestible medical device 100, besides patient identifier(s) and active agent identifier(s), based upon instructions from the prescribing physician and/or patient medical history. In some embodiments, the ingestible device identifier may include medication regimen information, which may be included in the active agent identifier, or separate therefrom. In some embodiments, the ingestible device identifier also includes a medication procedure, i.e., predetermined criteria under which a medication regimen may be modified or updated, and defined modifications or updates of the medication regimen upon occurrence of the predetermined criteria.

At 1004 the healthcare provider encodes a memory in communication with a processor of the ingestible medication device with the personal identifier and the active agent identifier. In one embodiment, the healthcare provider encodes the ingestible medication device while filling the prescription at the pharmacy. In another device, the healthcare provider encodes the ingestible medication device using a transport carrier that transports the ingestible medication device and other medications from the pharmacy to a caregiver station, wherein the transport carrier includes a wireless communication module.

In embodiments of step 1002 in which the processor of the healthcare provider obtains additional data from the ePrescribing system to be stored in ingestible medical device 100 besides patient identifier(s) and active agent identifier(s), at step 1004 the healthcare provider encodes a memory in communication with a processor of the ingestible medication device with this additional data.

At 1006, a caregiver device reads the personal identifier and the active agent identifier from memory of the ingestible medication device, or from the transport carrier.

At 1008 and 1012 the processor of the caregiver device carries out two comparisons of ingestible device identifiers with wristband identifiers stored on a patient wristband worn by a patient. In the first comparison, if the personal identifier 210 and the wristband patient identifier 262 do not match at 1008, the processor prevents 1010 the ingestible medication device from releasing the active agent.

If the personal identifier 210 successfully matches an wristband patient identifier 262 at 1008, the method proceeds to the second comparison at 1012. If the active agent identifier 220 and the wristband medication identifier 264 do not match at 1012, the processor prevents 1014 the ingestible medication device from releasing the active agent. If the active agent identifier 220 successfully matches the wristband medication identifier 264 at 1012, the caregiver administers the ingestible medication device to the patient wearing the patient wristband at 1016.

At 1018, the healthcare provider blockchain is updated to include a transaction for the prescribed ingestible medication device and its associated personal identifier and active agent identifier. The method 1000 then ends.

In embodiments of step 1002 in which the processor of the healthcare provider obtains additional data obtained from the ePrescribing system to be stored in ingestible medical device 100, besides patient identifier(s) and active agent identifier(s), one or more additional comparison is added to steps 1008 and 1012. In these embodiments, a successful match to wristband medication identifier also requires successfully matching the additional data from the ePrescribing system, such as medication regimen information. In these embodiments, the patient wristband label also stores the additional data from the ePrescribing system, such as medication regimen information for the patient wearing the patient wristband label.

While various aspects and embodiments have been disclosed, other aspects and embodiments are contemplated. The various aspects and embodiments disclosed are for purposes of illustration and are not intended to be limiting, with the true scope and spirit being indicated by the following claims.

The foregoing method descriptions and the interface configuration are provided merely as illustrative examples and are not intended to require or imply that the steps of the various embodiments must be performed in the order presented. As will be appreciated by one of skill in the art the steps in the foregoing embodiments may be performed in any order. Words such as "then," "next," etc. are not intended to limit the order of the steps; these words are simply used to guide the reader through the description of the methods. Although process flow diagrams may describe the operations as a sequential process, many of the operations can be performed in parallel or concurrently. In addition, the order of the operations may be re-arranged. A process may correspond to a method, a function, a procedure, a subroutine, a subprogram, etc. When a process corresponds to a function, its termination may correspond to a return of the function to the calling function or the main function.

The various illustrative logical blocks, modules, circuits, and algorithm steps described in connection with the embodiments disclosed here may be implemented as electronic hardware, computer software, or combinations of both. To clearly illustrate this interchangeability of hardware and software, various illustrative components, blocks, modules, circuits, and steps have been described above generally in terms of their functionality. Whether such functionality is implemented as hardware or software depends upon the particular application and design constraints imposed on the overall system. Skilled artisans may implement the described functionality in varying ways for each particular application, but such implementation decisions should not be interpreted as causing a departure from the scope of the present invention.

Embodiments implemented in computer software may be implemented in software, firmware, middleware, microcode, hardware description languages, or any combination thereof. A code segment or machine-executable instructions may represent a procedure, a function, a subprogram, a program, a routine, a subroutine, a module, a software package, a class, or any combination of instructions, data structures, or program statements. A code segment may be coupled to another code segment or a hardware circuit by passing and/or receiving information, data, arguments, parameters, or memory contents. Information, arguments, parameters, data, etc. may be passed, forwarded, or transmitted via any suitable means including memory sharing, message passing, token passing, network transmission, etc.

The actual software code or specialized control hardware used to implement these systems and methods is not limiting of the invention. Thus, the operation and behavior of the systems and methods were described without reference to the specific software code being understood that software and control hardware can be designed to implement the systems and methods based on the description here.

When implemented in software, the functions may be stored as one or more instructions or code on a non-transitory computer-readable or processor-readable storage medium. The steps of a method or algorithm disclosed here may be embodied in a processor-executable software module which may reside on a computer-readable or processor-readable storage medium. A non-transitory computer-readable or processor-readable media includes both computer storage media and tangible storage media that facilitate transfer of a computer program from one place to another. A non-transitory processor-readable storage media may be any available media that may be accessed by a computer. By way of example, and not limitation, such non-transitory processor-readable media may comprise RAM, ROM, EEPROM, CD-ROM or other optical disk storage, magnetic disk storage or other magnetic storage devices, or any other tangible storage medium that may be used to store desired program code in the form of instructions or data structures and that may be accessed by a computer or processor. Disk and disc, as used here, include compact disc (CD), laser disc, optical disc, digital versatile disc (DVD), floppy disk, and Blu-ray disc where disks usually reproduce data magnetically, while discs reproduce data optically with lasers. Combinations of the above should also be included within the scope of computer-readable media. Additionally, the operations of a method or algorithm may reside as one or any combination or set of codes and/or instructions on a non-transitory processor-readable medium and/or computer-readable medium, which may be incorporated into a computer program product.

What is claimed is:

1. A method comprising:
generating, by an ingestible medication device, an activation signal indicating ingestion of the ingestible medication device by a human subject, wherein the ingestible medication device contains an active agent designed to produce a physiological result in human beings, wherein a processor of the ingestible medication device is configured to generate a triggering signal to cause the ingestible medication device to release the active agent to the human subject;
in response to the activation signal, actuating, by the processor of the ingestible medication device, transmission of a limited range signal to an external device, wherein the external device is located no more than 3 m from the human subject;
determining, by the processor of the ingestible medication device, whether the ingestible medication device has received an external device identifier from the external device in response to the receipt by the external device of the limited range signal;
in response to a determination that the ingestible medication device has received the external device identifier from the external device, comparing, by the processor of the ingestible medication device, the external device identifier with an ingestible device identifier stored in the ingestible medication device comprising a personal identifier for the human subject and an active agent identifier for the active agent; and in the event the comparison of the ingestible device identifier with the external device identifier indicates that the human subject is authorized to receive the active agent, generating, by the processor of the ingestible medication device, the triggering signal to cause the ingestible medication device to release the active agent to the human subject and to communicate to a healthcare provider system a request to append a second medication-tracking blockchain to a first medication-tracking blockchain, wherein the first medication-tracking blockchain includes a first medication transaction representing the comparison of the ingestible device identifier with the external device identifier to indicate that the human subject is authorized to receive the active agent, and the second medication-tracking blockchain includes a second medication transaction representing the release of the active agent to the human subject, wherein both the first medication-tracking blockchain and the second medication-tracking blockchain include the personal identifier and the active agent identifier.

2. The method of claim 1, wherein the external device is a wristband including an RFID reader, and the ingestible device identifier is stored in an RFID marker within the ingestible medication device.

3. The method of claim 2, wherein the RFID marker within the ingestible medication device is a passive RFID device, further comprising the step, by the wristband including the RFID reader, of interrogating the RFID marker in response to receipt, by the RFID reader, of the activation signal indicating ingestion of the ingestible medication device by the human subject.

4. The method of claim 1, wherein the external device identifier comprises a wristband patient identifier, and wherein the comparing step compares the personal identifier to the wristband patient identifier to determine whether the wristband patient identifier identifies the same human subject as the personal identifier.

5. The method of claim 1, wherein the external device identifier comprises a wristband medication identifier, wherein the comparing step further compares the active agent identifier to the wristband medication identifier to determine whether the wristband medication identifier identifies the same active agent as the active agent identifier.

6. The method of claim 1, further comprising the step, by the processor of the ingestible medication device, in response to a determination that the ingestible medical device has not received the external device identifier from an external device in response to the receipt by the external device of the limited range signal, of preventing release of the active agent by the ingestible medication device.

7. The method of claim 1, further comprising the step, by the processor of the ingestible medication device, in response to a determination that the ingestible medical device has not received the external device identifier from an external device in response to the receipt by the external device of the limited range signal, of transmitting an out-of-range notification.

8. The method of claim 1, wherein the external device comprises a biosensor worn on or embedded in the body of the human subject configured to provide personal electrical signals of the human subject, configured to receive the limited range signal, and configured to communicate the external device identifier to the ingestible medication device.

9. The method of claim 1, wherein the external device identifier comprises a wristband patient identifier, wherein the first medication transaction represents the comparison of the ingestible device identifier with the wristband patient identifier to indicate that the human subject is authorized to receive the active agent.

* * * * *